United States Patent
Schroeppel et al.

(10) Patent No.: US 7,720,549 B2
(45) Date of Patent: May 18, 2010

(54) PARTIALLY IMPLANTABLE SYSTEM FOR THE ELECTRICAL TREATMENT OF ABNORMAL TISSUE GROWTH

(75) Inventors: Edward A Schroeppel, Sugar Land, TX (US); Mark Kroll, Simi Valley, CA (US); Kai Kroll, Minneapolis, MN (US)

(73) Assignee: Oncostim, Inc., Maple Grove, MN (US)

( * ) Notice: Subject to any disclaimer, the term of this patent is extended or adjusted under 35 U.S.C. 154(b) by 569 days.

(21) Appl. No.: 10/819,641

(22) Filed: Apr. 6, 2004

(65) Prior Publication Data
US 2005/0222623 A1  Oct. 6, 2005

(51) Int. Cl.
*A61N 1/18* (2006.01)

(52) U.S. Cl. ............................ 607/75; 607/2
(58) Field of Classification Search .................. 607/61, 607/1, 2, 33, 36
See application file for complete search history.

(56) References Cited

U.S. PATENT DOCUMENTS

| | | | |
|---|---|---|---|
| 4,003,379 A | 1/1977 | Ellinwood, Jr. | |
| 4,026,304 A | 5/1977 | Levy | |
| 4,289,135 A | 9/1981 | Nordenstrom et al. | |
| 4,572,214 A | 2/1986 | Nordenstrom et al. | |
| 4,639,244 A | 1/1987 | Rizk | |
| 4,679,561 A | 7/1987 | Doss | |
| 4,919,138 A | 4/1990 | Nordenstrom | |
| 4,974,595 A | 12/1990 | Nordenstrom | |
| 5,058,605 A | 10/1991 | Slovak | |
| 5,098,843 A | 3/1992 | Calvin | |
| 5,314,451 A | 5/1994 | Mulier | |
| 5,314,457 A * | 5/1994 | Jeutter et al. ................. 607/116 |
| 5,458,627 A | 10/1995 | Baranowski | |
| 5,501,662 A | 3/1996 | Hofmann | |
| 5,536,267 A | 7/1996 | Edwards et al. | |
| 5,584,872 A | 12/1996 | LaFontaine et al. | |
| 5,611,350 A * | 3/1997 | John ........................... 600/378 |
| 5,630,426 A * | 5/1997 | Eggers et al. ................ 600/547 |
| 5,674,267 A * | 10/1997 | Mir et al. ....................... 607/72 |
| 5,701,895 A * | 12/1997 | Prutchi et al. ................ 600/300 |
| 5,820,548 A * | 10/1998 | Sieben et al. ................ 600/361 |
| 5,919,187 A * | 7/1999 | Guglielmi et al. ............. 606/32 |
| 5,985,305 A | 11/1999 | Peery et al. | |
| 5,993,434 A | 11/1999 | Dev et al. | |
| 6,021,347 A * | 2/2000 | Herbst et al. ................... 607/2 |

(Continued)

OTHER PUBLICATIONS

PCT/US03/14104. International Search Report. Nov. 18, 2004.

(Continued)

*Primary Examiner*—Carl H. Layno
*Assistant Examiner*—Jon-Eric C. Morales
(74) *Attorney, Agent, or Firm*—Thomas F. Lebens; Sinsheimer Juhnke Leben & McIvor, LLP

(57) ABSTRACT

This present embodiment relates generally to the electrical treatment of malignant tumors and neoplasms by applying a voltage to affected tissue. Devices and various adaptations therein are described for use in electrical therapy. Additionally, various ambulatory devices are described which advantageously increase versatility of the electrical therapy system. The ambulatory devices may include an internal and external power source and/or a first and second power source. The ambulatory devices may also include communication means for communicating between various portions of the device.

6 Claims, 13 Drawing Sheets

U.S. PATENT DOCUMENTS

| | | | |
|---|---|---|---|
| 6,051,017 | A | 4/2000 | Loeb et al. |
| 6,169,924 | B1* | 1/2001 | Meloy et al. .................. 607/39 |
| 6,171,787 | B1 | 1/2001 | Wiley |
| 6,269,270 | B1* | 7/2001 | Boveja ......................... 607/45 |
| 6,278,895 | B1 | 8/2001 | Bernard |
| 6,366,808 | B1* | 4/2002 | Schroeppel et al. ............. 607/2 |
| 6,391,026 | B1* | 5/2002 | Hung et al. ................... 606/41 |
| 6,591,133 | B1 | 7/2003 | Joshi |
| 6,599,274 | B1 | 7/2003 | Kucharczyk et al. |
| 6,607,528 | B1* | 8/2003 | Quick et al. .................. 606/45 |
| 6,638,273 | B1* | 10/2003 | Farley et al. .................. 606/27 |
| 6,708,066 | B2 | 3/2004 | Herbst et al. |
| 6,713,291 | B2 | 3/2004 | King |
| 6,733,485 | B1* | 5/2004 | Whitehurst et al. ......... 604/500 |
| 6,738,663 | B2* | 5/2004 | Schroeppel et al. ............. 607/2 |
| 6,901,296 | B1* | 5/2005 | Whitehurst et al. .......... 607/50 |
| 2001/0021868 | A1 | 9/2001 | Herbst et al. |
| 2002/0026188 | A1* | 2/2002 | Balbierz et al. ............... 606/41 |
| 2002/0077676 | A1* | 6/2002 | Schroeppel et al. ........... 607/75 |
| 2003/0191504 | A1* | 10/2003 | Meadows et al. ............. 607/33 |
| 2004/0010290 | A1 | 1/2004 | Schroeppel et al. |
| 2004/0030334 | A1* | 2/2004 | Quick et al. .................. 606/45 |
| 2004/0172089 | A1* | 9/2004 | Whitehurst et al. ........... 607/45 |
| 2004/0254618 | A1 | 12/2004 | Schroeppel et al. |
| 2005/0004507 | A1 | 1/2005 | Schroeppel et al. |
| 2005/0222646 | A1 | 10/2005 | Schroeppel et al. |

OTHER PUBLICATIONS

PCT International Preliminary Report on Patentability, PCT/US2005/011430, date mailed Oct. 19, 2006.

U.S. Appl. No. 10/792,256, filed Mar. 2, 2004, Schroeppel.

U.S. Appl. No. 10/841,205, filed May 7, 2004, Schroeppel.

U.S. Appl. No. 10/881,375, filed Jun. 29, 2004, Schroeppel.

www.genetronics.com, retrieved Jul. 29, 2003.

Electro-Cancer Treatment, http://www.st-georg.com/ect.html, retrieved Oct. 25, 1999.

J. Belehradek, Jr., S. Orlowski, L.H. Ramirez, G. Pron, B. Poddevin, L.M. Mir. Electropermeabilization of Cells in Tissues Assessed by the Qualitative and Quantitative Electroloading of Bleomycin, Biochimica et Biophysica Acta 1190 (1994): 155-163.

M. Belehradek, C. Domenge, B. Luboinski, S. Orlowski, J. Belehradek, Jr., L.M. Mir. Abstract of Electrochemotherapy, a New Antitumor Treatrnent. First Clinical Phase I-II Trial, Cancer Dec. 15, 1993;72(12):3694-700.

J. Berendson and D. Simonsson. Electrochemical Aspects of Treatment of Tissue with Direct Current, European Journal of Surgery 1994; Suppl 574: 111-115.

K. Brandisky, I. Daskalov. Abstract of Electrical Field and Current Distributions in Electrochemotherapy, Bioelectrochemistry and Bioenergetics Feb. 1999;48(1):201-8.

H. Buchwald and T.D. Rohde. Implantable Pumps; Recent Progress and Anticipated Future Advances, ASAIO Journal 1992, p. 772-778.

M. Cemazar, G. Sersa and D. Miklavcic. Electrochemotherapy with Cisplatin in the Treatment of Tumor Cells Resistant to Cisplatin, Anticancer Research 18: 4463-4466 (1998).

B. Chen, Z. Xie, F. Zhu. Experimental Study on Electrochemical Treatment of Cancer in Mice, European Journal of Surgery, 1994; Suppl 574: 75-77.

C.K. Chou, J.A. McDougall, C. Ahn, N. Vora. Abstract of Electrochemical Treatment of Mouse and Rat Fibrosarcomas with Direct Current. Bioelectromagnetics 1997; 18(1):14-24.

B. Damascelli, G. Patelli, L.R. Frigerio, R. Lanocita, G. Di Tolla, A. Marchiano, C. Spreafico, F. Garbagnati, M.G. Bonalumi, L. Monfardini, V. Ticha, A. Prino. First Clinical Experience with a High-Capacity Implantable Infusion Pump for Continuous Intravenous Chemotherapy, CardioVascular and Interventional Radiology (1999) 22:37-43.

S. L. David, D.R. Absolom, C.R. Smith, J. Gams, and M.A. Herbert. Effect of Low Level Direct Current on In Vivo Tumor Growth in Hamsters, Cancer Research 45, 5625-5631, Nov. 1985.

R.A. Gatenby. Abstract of Mathmatical Models of Tumour Invasion Mediated by Transformation-Induced Alteration of Microenvironment pH, Symposium 240: The Tumour Microenvironment: Causes and Consequences of Hypoxia and Acidity, p. 2-3, held at the Novartis Foundation, London, 240 Oct. 10-12, 2000.

L.F. Glass, N.A. Fenske, M. Jaroszeski, R. Perrott, D.T. Harvey, D.S. Reintgen, R. Heller. Abstract of Bleomycin-Mediated Electrochemotherapy of Basal Cell Carcinoma, Journal of the American Academy of Dermatology Jan. 1996; 34(1):82-6.

H.Y. Gong, G.Z. Liu. Effect of Electrochemical Therapy on Immune Functions of Normal and Tumour-Bearing Mice, European Journal of Surgery, Suppl 1994; (574): 73-74.

S.A. Grossman, P.S. Staats. Abstract of Current management of pain in patients with cancer. Oncology (Huntingt) Mar. 1994; 8(3):93-107.

M.B. Habal, M.D., M.K. Schauble, M.D. Clinical Device Note: An Implantable DC Power Unit for Experimental Tumor Growth in Hamsters, Journal of the Association for the Advancement of Medical Instrumentation, vol. 7, No. 5, Nov.-Dec. 1973, p. 305-306.

M.B. Habal. Effect of Applied DC Currents on Experimental Tumor Growth in Rats, Journal of Biomedical Materials Research, vol. 14, 789-801 (1980).

M.A. Hamza, P.F. White, H.E. Ahmed, E.A. Ghoname. Abstract of Effect of the Frequency of Transcutaneous Electrical Nerve Stimulation on the Postoperative Opioid Analgesic Requirement and Recovery Profile. Anesthesiology Nov. 1999;91(5):1232-8.

C. Hauton, M. Charbonnier, L. Cara and J.P. Salles. A New Type of Liposome for Electrochemical Treatment of Cancer: The Lipogelosomes, European Journal of Surgery 1994; Suppl 574: 117-119.

K.T. Heruth. Medtronic SynchroMed Drug Administration System. Ann NY Acad Sci 1988: 531: 72-75.

G.A. Hofmann, S.B. Dev, S. Dimmer and G.S. Nanda. Electroporation Therapy: A New Approach for the Treatment of Head and Neck Cancer, IEEE Transactions on Biomedical Engineenng, vol. 46, No. 6, Jun. 1999.

G.A. Hofmann, S.B. Dev, G.S. Nanda and D. Rabussay. Electroporation Therapy of Solid Tumors, Critical Reviews in Therapeutic Drug Carrier Systems, 16(6):523-569 (1999).

C.E. Humphrey, E.H. Seal. Biophysical Approach Toward Tumor Regression in Mice, Science, vol. 130, 1959.

D.L. Kirsch, F.N. Lerner. Electromedicine: The Other Side of Physiology. In: "Innovations in Pain Management: A Practical Guide for Clinicians", selections of Chapter 23, 1995, GR Press, Winter Park, FL.

M. Kraus and B. Wolf. Implications of Acidic Tumor Microenvironment for Neoplastice Growth and Cancer Treatment: A Computer Analysis, Tumor Biology 1996; 17: 133-154.

M. Kraus and B. Wolf. Physicochemical Microenvironment as Key Regulator for Tumor Microevolution, Invasion, and Immune Response: Targets for Endocytotechmological Approaches in Cancer Treatment, Endocytobiosis & Cell Research, 12, 133-156 (1998).

Y.H. Lao, T.G. Ge, X.L. Zheng, J.Z. Zhang, Y.W. Hua, S.M. Mao and X. Feng. Electrochemical Therapy for Intermediate and Advanced Liver Cancer: A Report of 50 Cases, European Journal of Surgery 1994; Suppl 574: 51-53.

K.H. Li, Y.L. Xin, Y.N. Gu, B.L. Xu, D.J. Fan and B.F. Ni. Effects of Direct Current on Dog Liver: Possible Mechanisms for Tumor Electrochemical Treatment, Bioelectromagnetics 18:2-7 (1997).

X.Z. Lin, C.M. Jen, C.K. Choud, D.S. Chou, M.J. Sung, T.C. Chou. Saturated Saline Enhances the Effect of Electrochemical Therapy. Digestive Diseases and Sciences 2000;45(3): 509-514.

D. Liu, Y.L. Xin, B. Ge, F. Zhao, H.C. Zhso. Experimental Studies on Electrolytic Dosage of ECT for Dog's Oesophageal Injury and Clinical Effects of ECT for Oesophageal Anastomotic Opening Stenosis and Oesophageal Carcinoma, European Journal of Surgery Suppl 1994; (574):71-72.

Y. Matsushima, E. Takahashi, K. Hagiwara, C. Konaka, H. Miura, H. Kato and Y. Koshiishi. Clinical and Experimental Studies of Anti-Tumoural Effects of Electrochemical Therapy (ECT) Alone or in Combination with Chemotherapy, European Journal of Surgery 1994; Suppl 574: 59-67.

D. Miklavcic, D. An, J. Belehradek, Jr., L.M. Mir. Abstract of Host's Immune Response in Electrotherapy of Murine Tumors by Direct Current, European Cytokine Network Sep. 1997;8(3):275-9.

L.M. Mir, S. Orlowski, J. Belehradek Jr., and C. Paoletti. Electrochemotherapy Potentiation of Antitumour Effect of Bleomycin by Local Electric Pulses, European Journal of Cancer, vol. 27, No. 1, pp. 68-72, 1991.

D.M. Morris, M.D., A.A. Marino, Ph. D., and E. Gonzalez, M.D. Electrochemical Modification of Tumor Growth in Mice, Journal of Surgical Research 53, 306-309 (1992).

E. Nilsson. Modelling of the Electrochemical Treatment of Tumours, Dissertation, Department of Chemical Engineering and Technology, Applied Electrochemistry, Royal Institute of Technology, Stockholm 2000.

T. Nishi, S.B. Dev., K. Yoshizato, J. Kuratsu, Y. Ushio. Abstract of Treatment of Cancer Using Pulsed Electric Field in Combination With Chemotherapeutic Agents or Genes, Human Cell Mar. 1997;10(1):81-6.

B. Nordenstrom. Preliminary Clinical Trials of Electrophoretic Ionization in the Treatment of Malignant Tumors, IRCS Medical Science: Biomedical Technology; Cancer; Cell and Membrane Biology; Clinical Medicine; Respiratory System; Pathology, 6, 537 (1978).

B. Nordenstrom. Biologically Closed Electric Circuits; Clinical, Experimental and Theoretical Evidence for an Additional Circulatory Systems, XVI., Tissue transformations over BCEC in cancer of the breast, p. 203-268; XVII., Application of the principle of BCEC for treatment of cancer, p. 269-317. 1983, Karolinska Institutet, Stockholm. Sweden. Nordic Medical Publications.

B. Nordenstrom, M.D. Biologically Closed Electric Circuits: Activation of Vascular Interstitial Closed Electric Circuits for Treatment of Inoperable Cancers, Journal of Bioelectricity, 3 (1&2), 137-153 (1984).

B.E.W. Nordenstrom, M.D. Electrochemical Treatment of Cancer. I: Variable Response. American Journal of Clinical Oncology (CCT) 12(6): 530-536, 1989.

B.E.W. Nordenstrom, M.D., S. Eksborg, Ph. D., and H. Beving, Ph. D. Electrochemical Treatment of Cancer. II: Effect of Electrophoretic Influence on Adriamycin, American Journal of Clinical Oncology (CCT) 13(1): 75-88, 1990.

B.E.W. Nordenstrom, M.D. Survey of Mechanisms in Electrochemical Treatment (ECT) of Cancer, European Journal of Surgery 1994; Suppl 574: 93-109.

G.D. O'Clock, Ph. D. (E.E.), P.E. The Effects of In Vitro Electrical Stimulation on Eukaryotic Cells: Suppression of Malignant Cell Proliferation, Journal of Orthomolecular Medicine, vol. 12, No. 3, 1997.

M. Okino and H. Mohri. Effects of a High-Voltage Electrical Impulse and an Anticancer Drug on In Vivo Growing Tumors, Japan Journal of Cancer Research, (Gann) 78, 1319-1321; Dec. 1987.

S. Orlowski, J. Belehradek, Jr., C. Paoletti and L.M. Mir. Transient Electropermeablization of Cells in Culture; Increase of Cytotoxicity of Anticancer Drugs, Biochemical Pharmacology, vol. 37, No. 24, pp. 4727-4733, 1988.

W.R. Panje, M.P. Hier, G.R. Garman, E. Harrell, A. Goldman, I. Bloch. Abstract of Electroporation Therapy of Head and Neck Cancer, Annals of Otology, Rhinology and Laryngology Sep. 1998;107(9 Pt 1): 779-85.

A. Plesnicar, G. Sersa, L. Vodovnik, J. Jancar, L. Zaletel-Kragelj and S. Plesnicar. Electric Treatment of Human Melanoma Skin Lesions with Low Level Direct Electric Current: An Assessment of Clinical Experience Following a Preliminary Study in Five Patients, European Journal of Surgery 1994; Suppl 574: 45-49.

K.H. Quan. Analysis of the Clinical Effectiveness of 144 Cases of Soft Tissue and Superficial Malignant Tumours Treated with Electrochemical Therapy, European Journal of Surgery 1994; Suppl 574: 37-40.

N. Raghunand. Abstract of pH and Chemotherapy, Symposium 240: The Tumour Microenvironment: Causes and Consequences of Hypoxia and Acidity, p. 5-6, held at the Novartis Foundation, London, Oct. 10-12, 2000.

L.H. Ramirez, S. Orlowski, D. An, G. Bindoula, R. Dzodic, P. Ardouin, C. Bognel, J. Belehradek Jr., J-N Munck, and L.M. Mir. Electrochemotherapy on Liver Tumours in Rabbits, British Journal of Cancer (1998) 77(12). 2104-2111.

V.V. Ranade, Ph. D. Drug Delivery Systems 4. Implants in Drug Delivery, Journal of Clinical Pharmacology 1990;30:871-889.

A. Reis, T. Henninger. Zerstorung maligner Wachstumsenergie durch anodische Oxydation. Klin Wochenschrift 1951; _:39.

L. Samuelsson, J. Harnek, S.B. Ewers and L. Jonsson. Electrochemical and Megavolt Treatment of Rat Tumours, European Journal of Surgery 1994; Suppl 574: 69-70.

M.K. Schauble, M.B. Habal. Electropotentials of Tumor Tissues. Journal of Surgical Research 9: 9, 1969.

M.K. Schauble, M.B. Habal, H.D. Gullick. Inhibition of Experimental Tumor Growth in Hamsters by Small Direct Currents, Archives of Pathology and Laboratory Medicine.vol. 101, p. 294, Jun. 1977.

D.C. Schechter. Flashbacks: Containment of Tumors Through Electricity, Pacing and Clinical Electrophysiology, vol. 2, Jan.-Feb. 1979.

K. Seguchi, S. Kawauchi, Y. Morimoto, T. Arai, H. Asanuma, M. Hayakawa, M. Kikuchi. Abstract of Critical Parameters in the Cytotoxicity of Photodynamic Therapy Using a Pulsed Laser. Lasers Med Sci 2002;17(4):265-71.

D. Semrov, D. Miklavcic. Calculation of the Electrical Parameters in Electrochemotherapy of Solid Tumours in Mice, Computers in Biology and Medicine 28 (1998) 439-448.

G. Sersa, M. Cemazar, D. Miklavcic and D. J. Chaplin. Tumor Blood Flow Modifying Effect of Electrochemotherapy with Bleomycin, Anticancer Research 19: 4017-4022 (1999).

G. Sersa, Ph. D., S. Kranjc, B. Sc., and M. Cemazar, Ph. D. Improvement of Combined Modality Therapy with Cisplatin and Radiation Using Electroporation of Tumors, International Journal of Radiation-Oncology- Biology and Physics., vol. 46, No. 4, pp. 1037-1041, 2000.

B.N. Singh and C. Dwivedi. Antitumor Drug Delivery by Tissue Electroporation, Anti-Cancer Drugs 1999, 10, pp. 139-146.

Y. Song, C. Li, Y. Li, Q. Song, B. Chang, L. Song, C. Liu and T. Wang. Electrochemical Therapy in the Treatment of Malignant Tumours on the Body Surface, European Journal of Surgery 1994; Suppl 574: 41-43.

L.C. Song, C.Y. Liu, B.P. Zhang, T. Wang, Y.Q. Song and Y.W. Li. Electrochemical Therapy (ECT) for Thyroid Adenoma During Acupuncture Anaesthesia: Analysis of 46 Patients, European Journal of Surgery 1994; Suppl 574: 79-81.

S. Srinivasan, G.L. Gahen Jr., G.E. Stoner. Electrochemistry in The Biomedical Sciences. In: Bloom H, Gumann F (eds): Electrochemistry The Last Thirty and The Next Thirty Years. New York: Plenum Press, 177.

T.V. Taylor, P. Engler, B.R. Pullan and S. Holt. Ablation of Neoplasia by Direct Current, British Journal of Cancer (1994), 70, 342-345.

A. Turler, H. Schaeer, N. Schaefer, D. Maintz, M. Wagner, J.C. Qiao and A.H. Hoelscher. Local Treatment of Hepatic Metastases with Low-Level Direct Electric Current: Experimental Results, Scandinavian Journal of Gastroenterology Mar. 2000;35(3):322-328.

A.L. Vandenbogaerde, E.M. Delaey, A.M. Vantieghem, B.E. Himpens, W.J. Merlevede P.A. de Witte. Abstract of Cytotoxicity and Antiproliferative Effect of Hypericin and Derivatives After Photosensitization. Photochem Photobiol Jan. 1998;67(1):119-25.

P. Vaupel, D.K. Kelleher, M. Hockel. Abstract of Oxygen Status of Malignant Tumors: Pathogenesis of Hypoxia and Significance for Tumor Therapy. Semin Oncol Apr. 2001; 28(2 Suppl 8):29-35.

L. Vodovnik, D. Miklavcic, G. Sersa. Modified Cell Proliferation Due to Electrical Currents, Medical and Biological Engineering and Computing, 1992, 30, CE21-CE28.

N.J. Vogelzang, M. Ruane, and T.R. DeMeester. Phase I Trial of an Implanted Battery-Powered, Programmable Drug Delivery System for Continuous Doxorubicin Administration, Journal of Clinical Oncology, vol. 3, No. 3 Mar. 1985.

H. von Euler. Electrochemical Treatment of Tumours, Doctoral Thesis, Uppsala 2002, Swedish University of Agricultural Sciences.

H.L. Wang. Electrochemical Therapy of 74 Cases of Liver Cancer, European Journal of Surgery 1994; Suppl 574: 55-57.

J.C. Weaver. Electroporation: A General Phenomenom for Manipulating Cells and Tissues. J Cell Biochem 1993; 51 No. 4: 426-435.

B.D. Wigness, F.D. Dorman, H.J. Robinson, E.A. Arendt, T.R. Oegema Jr., T.D. Rohde, and H. Buchwald. Catheter with an Anchroring Tip for Chronic Joint Capsule Perfusion, ASAIO Trans. Jul.-Sep. 1991; 37(3): M290-2.

M. Wojcicki, R. Kostyrka, B. Kaczmarek, J. Kordowski, M. Romanowski, M. Kaminski, J. Klonek, S. Zielinski. Abstract of Electrochemical Therapy in Palliative Treatment of Malignant Dysphagia: A Pilot Study, Hepatogastroenterology Jan.-Feb. 1999;46(25):278-84.

B. Wolf, M. Kraus and U. Sieben. Potential of Microsensor-Based Feedback Bioactuators for Biophysical Cancer Treatment, Biosensors & Bioelectronics vol. 12, No. 4, pp. 301-309, 1997.

B. Wolf, M. Brischwein, W. Baumann, R. Ehret, T. Henning, M. Lehmann, A. Schwinde. Microsensor-Aided Measurements of Cellular Signalling and Metabolism on Tumor Cells, Tumor Biology 1998; 19:374-383.

Y.L. Xin, D. Liu. Electrostatic Therapy (EST) of Lung Cancer and Pulmonary Metastasis: Report of 15 Cases, European Journal of Surgery 1994; Suppl 574: 91-92.

Y.L. Xin. Organisation and Spread of Electrochemical Therapy (ECT) in China, Honorary Lecture. European Journal of Surgery 1994; Suppl 577: 25-30.

Y.L. Xin, F.Z. Xue, B.S. Ge, F.R. Zhao, B. Shi and W. Zhang. Electrochemical Treatment of Lung Cancer, Bioelectromagnetics 18:8-13 (1997).

Y.L. Xin, F.Z. Xue, F.G. Zhao. Effectiveness of Electrochemical Therapy in the Treatment of Lung Cancers of Middle and Late Stage, Chinese Medical Journal 1997; 110(5): 379-383.

Y. Yen, J.R. Li, B.S. Zhou, F. Rojas, J. Vu and C.K. Chou. Electrochemical Treatment of Human KB Cells In Vitro, Bioelectromagnetics 20:34-41 (1999).

M. Yokoyama, T. Itaoka, H. Nakajima, T. Ikeda, T. Ishikura, S. Nitta. Abstract of the Use of Direct Current in the Local Destruction of Cancer Tissues, Gan to Kagaku Ryoho Apr. 1989:16(4 Pt 2-2):1412-1417.

European Examination Report for Application No. EP05733003.7 issued Apr. 21, 2009.
Office Action from U.S. Appl. No. 10/434,400 dated Jul. 12, 2007.
Examiner Interview Summary PTOL-413 from U.S. Appl. No. 10/434,400 dated Jul. 13, 2006.
Office Action from U.S. Appl. No. 10/434,400 dated Feb. 14, 2006.
International Search Report, PCT/US2003/014104, mail date Jan. 27, 2005.
Notice of Allowance from U.S. Appl. No. 09/524,405 dated Sep. 26, 2001.
Office Action from U.S. Appl. No. 09/524,405 dated May 22, 2001.
Notice of Allowance from U.S. Appl. No. 09/974,474 dated Dec. 22, 2003.
Office Action from U.S. Appl. No. 09/974,474 dated Jul. 11, 2003.
Office Action from U.S. Appl. No. 10/881,375 dated Apr. 11, 2007.
Office Action U.S. Appl. No. 10/881,375 dated Sep. 13, 2006.
Office Action U.S. Appl. No. 10/792,256 dated Jun. 25, 2007.
Office Action U.S. Appl. No. 10/841,205 dated Nov. 6, 2006.
Office Action U.S. Appl. No. 09/974,474 dated Apr. 29, 2003.
European Patent Office, Office Action for 05 733003.7 mailed Aug. 13, 2008.
Final Office Action for U.S. Appl. No. 10/881,375 mailed Oct. 31, 2008.
Non-Final Office Action from U.S. Appl. No. 10/792,256 mailed Apr. 30, 2009.
Final Office Action from U.S. Appl. No. 10/841,205 mailed May 4, 2009.
Non-Final Office Action from U.S. Appl. No. 10/881,375 mailed Jun. 9, 2009.
Non-Final Office Action from U.S. Appl. No. 10/841,205 mailed Feb. 2, 2010.
Notice of Allowance from U.S. Appl. No. 10/792,256 mailed Feb. 12, 2010.

* cited by examiner

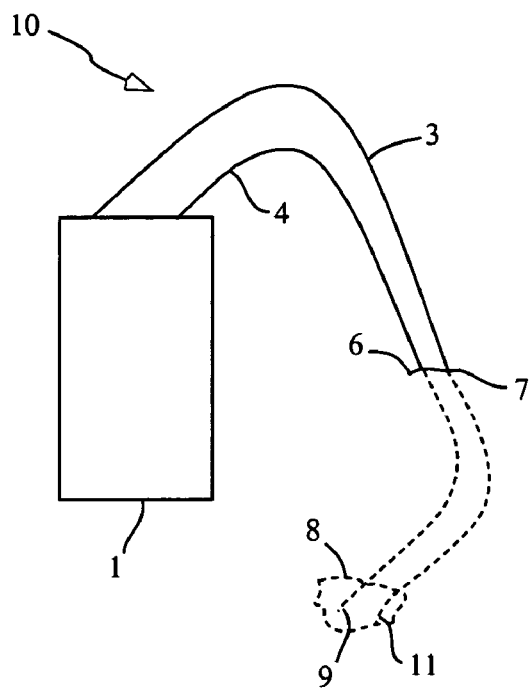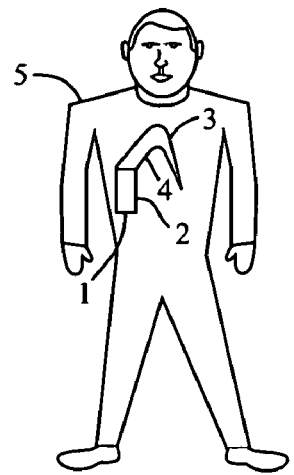
Fig. 1A                Fig. 1B
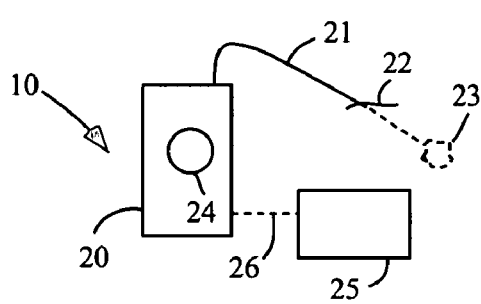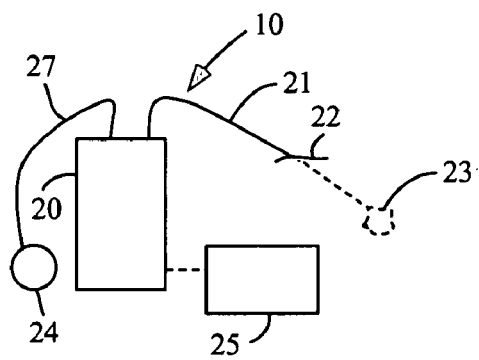
Fig. 2A                Fig. 2B
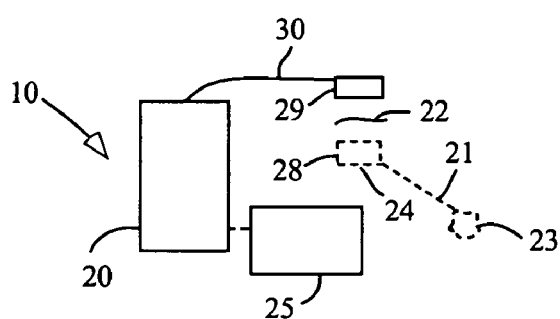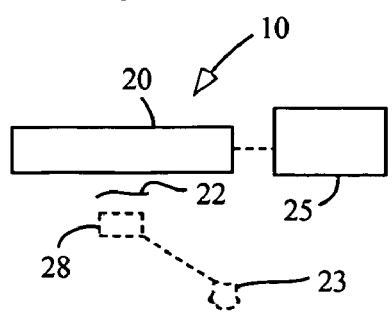
Fig. 2C                Fig. 2D

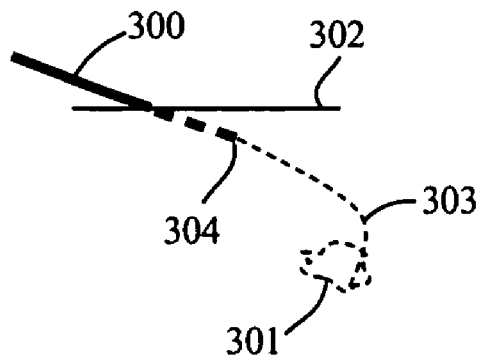 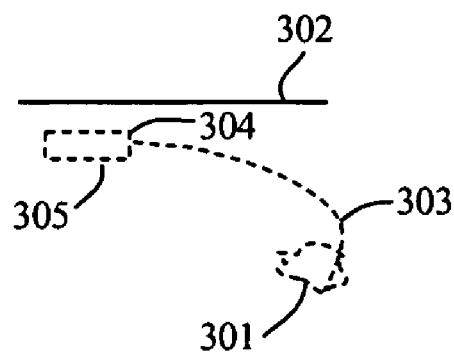
Fig. 7A  Fig. 7B
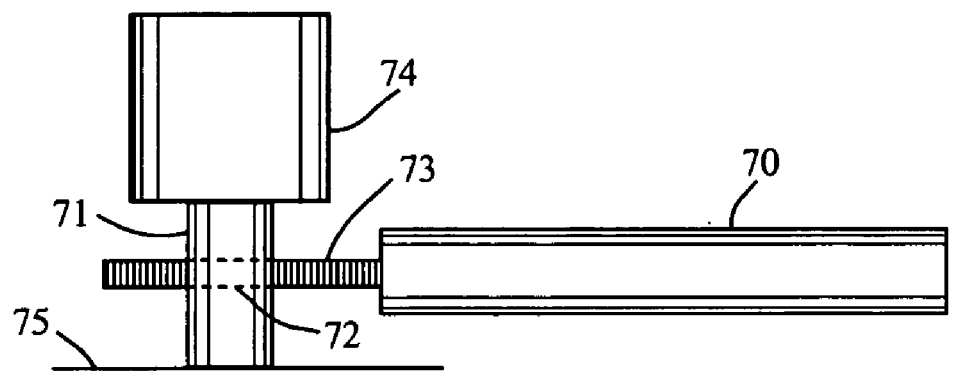
Fig. 8

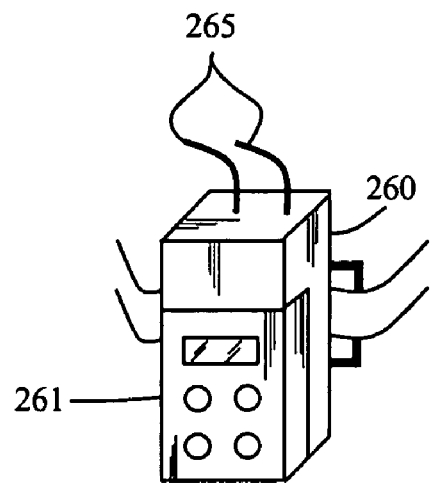 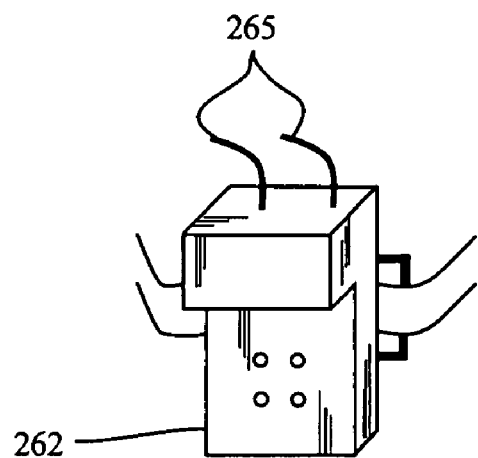
Fig. 16A        Fig. 16B
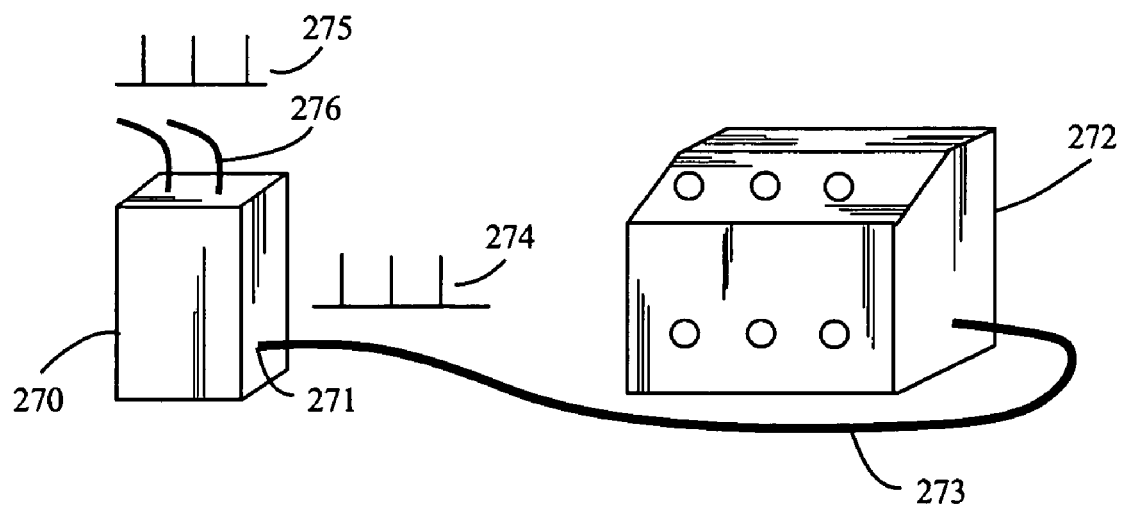
Fig. 17

US 7,720,549 B2

PARTIALLY IMPLANTABLE SYSTEM FOR THE ELECTRICAL TREATMENT OF ABNORMAL TISSUE GROWTH

RELATED APPLICATIONS

This application is related to U.S. Ser. No. 10/434,400 for "METHOD AND DEVICE FOR TREATING CANCER IN CONJUNCTION WITH CHEMOTHERAPEUTIC AGENTS AND RADIATION THERAPY" filed May 7, 2003, which is a CIP of U.S. Ser. No. 09/974,474 for "IMPLANTABLE DEVICE AND METHOD FOR THE ELECTRICAL TREATMENT OF CANCER" filed Oct. 9, 2001, which is a non-provisional application of provisional U.S. Ser. No. 60/238,609 for "IMPLANTABLE THERAPEUTIC DEVICE" filed Feb. 13, 2001, all of which are hereby incorporated by reference.

U.S. Ser. No. 10/434,400 for "METHOD AND DEVICE FOR TREATING CANCER IN CONJUNCTION WITH CHEMOTHERAPEUTIC AGENTS AND RADIATION THERAPY" filed May 7, 2003 is also a non-provisional application claiming the benefit of provisional U.S. Ser. Nos. 60/377,840 for "PROGRAMMER AND INSTRUMENT FOR ELECTROCHEMICAL CANCER TREATMENT" filed May 7, 2002; 60/377,841 for "METHOD OF ELECTRICAL TREATMENT FOR CANCER IN CONJUNCTION WITH CHEMOTHERAPY AND RADIOTHERPAY filed May 7, 2002; 60/378,209 for "LEAD CONDUIT METHOD FOR ECT THERAPY" filed May 7, 2002; 60/378,210 for "DIELECTRIC SENSOR FOR ELECTROCHEMICAL CANCER THERAPY" filed May 7, 2002; 60/378,211 "INDIVIDUALLY IDENTIFIABLE ELECTRODES FOR ELECTROCHEMICAL CANCER THERAPY" filed May 7, 2002; 60/378,212 for "MULTIPLE TUMOR TREATMENT FOR CANCER BY ELECTRICAL THERAPY" filed May 7, 2002; 60/378,213 for "PATIENT CONTROL FOR ELECTROCHEMICAL CANCER THERAPY" filed May 7, 2002; 60/378,214 for "OPTICAL FIBER ECT SYSTEM FOR PHOTOACTIVATED CYTOTOXIC DRUGS" filed May 7, 2002; 60/378,215 for "SPECIALIZED LEAD FOR ELECTROCHEMICAL CANCER TREATMENT" filed May 7, 2002; 60/378,216 "THREE-AXIS ELECTRODE SYSTEM TO CHASE THE CENTER OF TUMOR MASS" filed May 7, 2002; 60/378,629 for "CLOSED LOOP OPERATION OF ELECTROCHEMICAL TREATMENT FOR CANCER" filed May 9, 2002; 60/378,824 for "METHOD OF IMAGING BEFORE AND AFTER ELECTROCHEMICAL TREATMENT" filed May 9, 2002; 60/379,793 for "ECT AND ELECTROPORATION ELECTRODE SYSTEM" filed May 13, 2002; 60/379,797 for "FIXATION MEANS LOCATED OUTSIDE TUMOR MASS FOR ECT FOR CANCER" filed May 13, 2002; and 60/469,205 for "METHOD AND DEVICE FOR TREATING CANCER WITH ELECTRICAL THERAPY IN CONJUNCTION WITH CHEMOTHERAPEUTIC AGENTS AND RADIATION THERAPY" filed May 8, 2003, all of which are hereby incorporated by reference.

This application is also related to Ser. No. 09/524,405 for "IMPLANTABLE DEVICE AND METHOD FOR THE ELECTRICAL TREATMENT OF CANCER" filed Mar. 13, 2000, now U.S. Pat. No. 6,366,808, and provisional U.S. Ser. Nos. 60/238,612 for "ELECTROPHORETIC DRUG INFUSION DEVICE" filed Oct. 10, 2000; and 60/255,184 for "METHOD FOR ELIMINATING POSSIBLE CORROSION OF ELECTRODES IN ELECTROCHEMICAL THERAPY AND ELECTROCHEMOTHERAPY" filed Dec. 12, 2000; and 60/128,505 for "IMPLANTABLE DEVICE AND METHOD FOR THE ELECTRICAL TREATMENT OF CANCER" filed Apr. 9, 1999, all of which are herein incorporated by reference.

BACKGROUND OF THE INVENTION

1. Field of the Invention

This invention relates generally to the electrical treatment of malignant tumors and neoplasms by applying a voltage to affected tissue. Devices and various adaptations therein are described for use in electrical therapy. For example, a partially implantable device is described wherein one or more leads (a.k.a. wires) containing one or more electrodes are implanted into a patient having a tumor. Coupled to the lead or leads is a generator for supplying power to the electrode or electrodes. A portion of the generator may or may not be implanted into the patient.

2. Discussion of the Related Art

Cancer is one of the major causes of hospitalization and death worldwide. However, many of the therapies applied to cancer treatment are either ineffective or not well-tolerated by patients.

Cancer malignancies result in approximately 6,000,000 deaths worldwide each year. In 1995, 538,000 cancer related deaths were reported in the United States, representing over 23% of the total deaths in the United States. This number has increased since 1970 when 331,000 deaths occurred. The estimated number of new cases in the United States in 1997 was 1,382,000. An astounding 40% of Americans will eventually be stricken with the disease and more than 1 in 5 will die from it. The percentage is increasing at about 1% per year and cancer deaths will soon outstrip deaths from heart disease.

Much of the medical care cost associated with cancer results from hospitalization. In 1994 there were 1,226,000 hospital discharges in the United States related to cancer treatment. The cost of cancer in terms of both human suffering and monetary expenditures is staggering. Effective treatment methods, which result in fewer days of hospital care, are desperately needed.

Primary treatment methods currently used in cancer therapy include surgery, radiation therapy, chemotherapy, hormone therapy and many others including bone marrow replacement, biological response modifiers, gene therapy, and diet. Therapy often consists of combinations of these treatment methods. It is well known that these methods may result in sickness, pain, disfigurement, depression, spread of the cancer, and ineffectiveness. Despite recent announcements of potential pharmaceutical "cures", which may work well in animals and in humans in certain cases, researchers are cautious in overstating their effectiveness. In the case of radiation treatment, rapid decreases in the size of poorly differentiated tumors after treatment may be experienced; however, shortly thereafter the tumor often experiences re-growth. Unfortunately, following re-growth the tumor is generally more insensitive to future radiation treatment attempts.

The approaches previously described, as well as other prior approaches, are not sufficient to meet the needs of real patients. The present invention addresses the above and other needs.

SUMMARY OF THE INVENTION

This invention relates generally to a method of treating cancer. It involves an ambulatory device, which may have an implantable portion and an external portion, consisting of one or more power sources and one or more wires (or leads) containing one or more electrodes. The electrodes are implanted in or near the tumor and a power source (or generator), or portion thereof, may be implanted subcutaneously as close to the tumor as practical. The device may be powered by an implanted power supply and/or an external electrical source. The implantation is typically performed under local anesthesia and at least a portion of the device is generally left implanted for a period of months. With implantation, the device permits electric current to be applied at low levels for long periods of time. In another embodiment, the implanted device may be connected to an external device for energy input, data input, and/or therapy regimen modifications. While the internal generator is useful for applying low levels of electrical current for long periods of time, the external electrical source may be advantageously used to generate high levels of electrical current over shorter periods of time. In a preferred embodiment the external generator (or power source) may produce currents and pulses useful in electroporation therapy. In a preferred embodiment, electricity is provided in the form of direct current.

In one embodiment, a medical device for the treatment of cancer comprising an implantable portion, an external portion, and an affixing means for securing the external portion is described. In a preferred embodiment, the affixing means may be any method useful for affixing or attaching the external portion to an object, such as, for example, a patient, a patient's bed, and an IV bracket. Examples of methods for affixing the external portion to an object include strapping, snapping, tying, and "velcroing" the external portion to the object. In another embodiment, the external portion may be placed in an external portion containing apparatus, such as, for example, a pouch, or like apparatus. Furthermore, the pouch, or like apparatus, may be affixed to an object by various methods such as strapping, snapping, tying, and velcroing; the external portion may then be secured (or affixed) to an object by way of a external portion containing apparatus, such as for example a pouch, satchel, and the like. The external portion, and external portion containing apparatus, may be designed such that the external portion makes electrical contact with the skin of a patient.

The implantable portion is further described as having a device housing, circuitry contained within the device housing, and at least one electrode operably coupled to the circuitry wherein the circuitry delivers electrical therapy to the at least one electrode for the treatment of cancerous tumors.

The external portion is described as having a means for interacting with the implantable portion. The interacting means may be any of a hardwire connection and a wireless connection. The interacting means may control the implantable portion, provide power to the implantable portion, monitor the implantable portion, receive data from the implantable portion, and/or dispense drugs to the implantable portion. Furthermore, any data collected from the implantable portion may be formatted into an oncogram by, in one example, the external portion.

In another embodiment, the implantable portion of the medical device may include a power source. The power source may be, in one example, a battery. The power source may or may not be rechargeable. In the case of a rechargeable power source, however, the external portion may recharge the implantable power source.

In yet another embodiment, described is a medical device for the treatment of cancer comprising an implantable portion having a device housing, circuitry contained within the device housing, and at least one electrode operably coupled to said circuitry wherein the circuitry delivers electrical therapy to the at least one electrode for the treatment of cancerous tumors; an external portion having a means for providing power to the implantable portion; and an affixing means for securing the external portion.

The means for providing power may be any of a hardwire connection and/or a wireless connection. Affixing means are similar to those described hereinabove.

The medical device may also have a communication means for communicating between the implantable portion and the external portion. Communication means may be any of a hardwire connection and/or a wireless connection. In any case, the communication means may transfer data from either the external portion to the internal portion or vice versa. Data collected (or received) by the external portion may be formatted into an oncogram.

In yet another embodiment, described is a medical device for the treatment of cancer comprising an implantable portion having a device housing, a port for receiving power, circuitry contained within the device housing wherein the circuitry is coupled to the port for receiving power, and at least one electrode operably coupled to the circuitry wherein the circuitry delivers electrical therapy to the at least one electrode for the treatment of cancerous tumors; an external portion having circuitry contained within the external portion wherein the circuitry is coupled to a power source; a wire operably coupled to the circuitry of the external portion and the port for receiving power of the implantable portion wherein the wire transports power from the external portion to the implantable portion; and an affixing means for securing the external portion.

In another embodiment, the medical device may further comprise a connecting means for quickly coupling and uncoupling said external portion to said port for receiving power. In one example, the connecting means may consist of at least one pin connector in the removable external portion which is adapted to fit into at least one port of similar size.

In yet another embodiment, a medical device for the treatment of cancer comprising an external generator for providing power, at least one electrode transcutaneously placed in a body wherein the at least one electrode is operably coupled to the external generator such that the at least one electrode delivers electrical therapy to body tissue, and an affixing means for securing the external generator is described.

In a preferred embodiment, the external portion may be secured to, for example, a patient, a patient's bed, and an IV bracket.

In another embodiment, the external portion may be adapted to make electrical contact with the skin of a patient.

In another embodiment, the medical device may further comprise an external portion containing apparatus.

In another embodiment, the medical device may further comprise an implantable portion positioned electrically between the electrode and the external portion.

In yet another embodiment, a method of treating cancerous tumors comprising the steps of implanting at least one electrode into the tumor, coupling a source of electrical power to the electrode, delivering electrical therapy into the tumor, and securing the external generator is described.

In another embodiment, the method further comprises the step of adding a second source of electrical power between the electrode and the source of electrical power wherein the second source of electrical power may be implanted.

BRIEF DESCRIPTION OF THE DRAWINGS

The above mentioned and other objects and features of this invention and the manner of attaining them will become apparent, and the invention itself will be best understood by reference to the following description of the embodiments of the invention in conjunction with the accompanying drawings, wherein:

FIGS. 1a and 1b are schematic representations of a partially implantable device;

FIGS. 2a, 2b, 2c, and 2d are drawings of additional examples of partially implantable devices;

FIGS. 7a and 7b are representations of lead designs useful with the devices described herein;

FIG. 8 is an illustration of a fixation means useful for use with the devices described herein;

FIGS. 16a and 16b are depictions of an external generator with a removable section;

FIG. 17 is a drawing of an external generator having an input connector;

DETAILED DESCRIPTION OF THE PREFERRED EMBODIMENT

Figure 3:
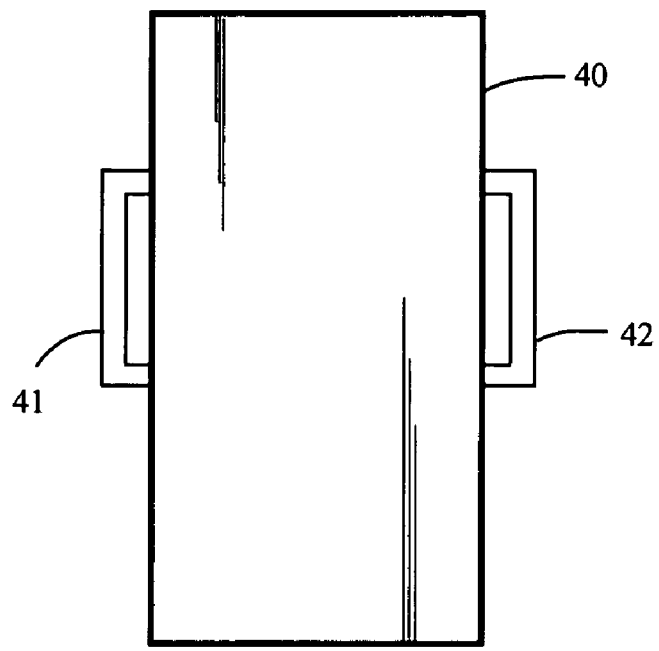
FIG. 3 is a drawing of an external generator suitable for use with any of FIGS. 1 and 2a-2d.

The following description is of the best mode presently contemplated for practicing the invention. This description is not to be taken in a limiting sense, but is made merely for the purpose of describing the general principles of the invention. The scope of the invention should be ascertained with reference to the claims.

The devices and methods of the present embodiment are contemplated for use in patients afflicted with cancer or other non-cancerous (benign) growths. These growths may manifest themselves as any of a lesion, polyp, neoplasm (e.g. papillary urothelial neoplasm), papilloma, malignancy, tumor (e.g. Klatskin tumor, hilar tumor, noninvasive papillary urothelial tumor, germ cell tumor, Ewing's tumor, Askin's tumor, primitive neuroectodermal tumor, Leydig cell tumor, Wilms' tumor, Sertoli cell tumor), sarcoma, carcinoma (e.g. squamous cell carcinoma, cloacogenic carcinoma, adenocarcinoma, adenosquamous carcinoma, cholangiocarcinoma, hepatocellular carcinoma, invasive papillary urothelial carcinoma, flat urothelial carcinoma), lump, or any other type of cancerous or non-cancerous growth. Tumors treated with the devices and methods of the present embodiment may be any of noninvasive, invasive, superficial, papillary, flat, metastatic, localized, unicentric, multicentric, low grade, and high grade.

The devices and methods of the present embodiment are contemplated for use in numerous types of malignant tumors (i.e. cancer) and benign tumors. For example, the devices and methods described herein are contemplated for use in adrenal cortical cancer, anal cancer, bile duct cancer (e.g. periphilar cancer, distal bile duct cancer, intrahepatic bile duct cancer), bladder cancer, benign and cancerous bone cancer (e.g. osteoma, osteoid osteoma, osteoblastoma, osteochrondroma, hemangioma, chondromyxoid fibroma, osteosarcoma, chondrosarcoma, fibrosarcoma, malignant fibrous histiocytoma, giant cell tumor of the bone, chordoma, lymphoma, multiple myeloma), brain and central nervous system cancer (e.g. meningioma, astocytoma, oligodendrogliomas, ependymoma, gliomas, medulloblastoma, ganglioglioma, Schwannoma, germinoma, craniopharyngioma), breast cancer (e.g. ductal carcinoma in situ, infiltrating ductal carcinoma, infiltrating lobular carcinoma, lobular carcinoma in situ, gynecomastia), Castleman disease (e.g. giant lymph node hyperplasia, angiofollicular lymph node hyperplasia), cervical cancer, colorectal cancer, endometrial cancer (e.g. endometrial adenocarcinoma, adenocanthoma, papillary serous adnocarcinoma, clear cell), esophagus cancer, gallbladder cancer (mucinous adenocarcinoma, small cell carcinoma), gastrointestinal carcinoid tumors (e.g. choriocarcinoma, chorioadenoma destruens), Hodgkin's disease, non-Hodgkin's lymphoma, Kaposi's sarcoma, kidney cancer (e.g. renal cell cancer), laryngeal and hypopharyngeal cancer, liver cancer (e.g. hemangioma, hepatic adenoma, focal nodular hyperplasia, hepatocellular carcinoma), lung cancer (e.g. small cell lung cancer, non-small cell lung cancer), mesothelioma, plasmacytoma, nasal cavity and paranasal sinus cancer (e.g. esthesioneuroblastoma, midline granuloma), nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma (e.g. embryonal rhabdomyosarcoma, alveolar rhabdomyosarcoma, pleomorphic rhabdomyosarcoma), salivary gland cancer, skin cancer (e.g. melanoma, nonmelanoma skin cancer), stomach cancer, testicular cancer (e.g. seminoma, nonseminoma germ cell cancer), thymus cancer, thyroid cancer (e.g. follicular carcinoma, anaplastic carcinoma, poorly differentiated carcinoma, medullary thyroid carcinoma, thyroid lymphoma), vaginal cancer, vulvar cancer, and uterine cancer (e.g. uterine leiomyosarcoma).

Patients treated with the devices and methods of the present embodiment may be any living thing, but preferably a mammal such as, but not limited to, humans, monkeys, chimps, rabbits, rats, horses, dogs, and cats. Patients treated with the devices and methods of the present embodiment may be of any age (e.g. infant, child, juvenile, adolescent, adult, and even pregnant women and their unborn fetus, such as in the case of gestational trophoblastic disease).

The devices and methods of the present embodiment work to treat cancerous tumors by delivering electrical therapy continuously and/or in pulses for a period of time ranging from a fraction of a second to several days, weeks, and/or months to tumors. In a preferred embodiment, electrical therapy is direct current (DC) electrical therapy. However, electrical therapy may also be in the form of alternating current (AC) electrical therapy. Additionally, electrical therapy may be direct current electrical therapy modified to mimic the output waveform of an alternating current. For the purposes of discussion herein, "electrical therapy" refers to the application of electrical current, in DC and/or AC, in any waveform, to biological material.

Modified DC output can be achieved in several ways. For example, common scenarios include Pulse Width Modulation (PWM) and Pulse Frequency Modulation (PFM). In PWM schemes, frequency is constant, but pulse width varies (where duty cycle=pulse width/period). In the PFM scenario, pulse width is fixed, but the frequency (i.e. period) varies. In either case, i.e. PWM and PFM, at least one of the variables in the equation of duty cycle=pulse width/period is adjusted.

Duty cycle can range anywhere between 0 and 100%. In one example, a 2 volt output can be achieved by chopping the output of a 3 volt energy source (e.g. battery) with a 66% duty cycle. The duty cycle may be reduced to 66% by turning the 3 volt energy source on for 2 ms and then off for 1 ms, sequentially. Therefore, the resulting or "effective" DC output is approximately two thirds of the possible maximum direct current output.

Both PWM and PFM can be used to increase the efficiency of a system utilizing an output less than maximum since switches (transistors) lose significant power when they are only partially turned on. However, very little power is lost when the switches (transistors) are either completely on or off. In the case of PWM and PFM, power is completely on or off, but because the duty cycle is altered as a result of either pulse width or frequency the system can provide an output less than the maximum output allowed by the energy source at a 100% duty cycle.

For the purposes of discussion herein, the term "direct current (DC) electrical therapy" may be used interchangeably with "direct current (DC) ablation". Additionally, for the purposes of discussion herein, the term "electrical therapy" may refer to any amount of charge, voltage, and/or current delivered to a patient in any period of time in AC, DC, or a modified variation thereof. For example, charge, voltage, and/or current used at levels sufficient for DC ablation (which are generally lower charge, voltage, and/or current and longer periods of time) and charge, voltage, and/or current used at levels sufficient for electroporation (which are generally higher charge, voltage, and/or current and shorter periods of time) are both included in "electrical therapy". A "low" level of voltage may, for example, be in the range lower than 0.5 V. A "high" level of voltage may, for example, be in the range higher than 50 V. In a preferred embodiment, "high" voltage may be in the range of 50 V to 1500 V. A "moderate" or "medium" level of voltage may, for example, be in the range of 0.5 V to 50 V. Furthermore, "electroporation" (i.e. rendering cellular membranes permeable) as used herein may be caused by any amount of charge, voltage, and/or current delivered to a patient in any period of time sufficient to open holes in cellular membranes (e.g. to allow diffusion of molecules such as pharmaceuticals, solutions, genes, and other agents into a viable cell).

Delivering electrical therapy to tissue causes a series of biological and electrochemical reactions. At a high enough voltage, cellular structures and cellular metabolism are severely disturbed by the application of electrical therapy. Although both cancerous and non-cancerous cells are destroyed at certain levels of electrical therapy, tumor cells are more sensitive to changes in their microenvironment than are non-cancerous cells. Distributions of macroelements and microelements are changed as a result of electrical therapy.

Electrical therapy produces various byproducts including hydrogen, oxygen, chlorine, and hydrogen peroxide. Hydrogen peroxide is known to destroy living tissues whereas the effect of the other reaction products on living tissues varies. The byproducts and changes in tissue that result from electrical therapy are differentially experienced throughout the tissue based on the positioning of the anode and cathode. For example, chlorine, which is a strong oxidant, is liberated at the anode, whereas hydrogen is liberated at the cathode. Additionally, the concentration of chlorine ions is high around the anode while the concentration of sodium and potassium ions is found to be higher around the cathode. pH changes due to electrical therapy cause the tissue around the anode to become strongly acidic, down to 2.1, while the tissue around the cathode becomes strongly basic, up to 12.9. Water migrates from the anode to the cathode while fat moves from the cathode to the anode, causing local hydration around the cathode and dehydration around the anode. Proteins may be denatured in electrical therapy. For example, hemoglobin is transformed into acidic hemoglobin around the anode and alkaline hemoglobin around the cathode.

Electrochemical reactions as a function of pH and electrode potential can be predicted by means of a Pourbaix diagram in *Aqueous Solutions*—Pergamon Press, 1986—by Pourbaix, which is herein incorporated by reference.

As is readily understood by those of ordinary skill in the art, the coulomb (C) is the basic unit of charge (e.g. the magnitude of the charge on an electron or a proton is $1.6 \times 10^{-19}$ coulombs—where the charge on an electron is negative and the charge on a proton is positive). Electrical therapy may be described as the application of voltage in volts (V), current in amperes (A), and/or total coulombs (C) delivered. Voltage is a measure of force per unit of charge. Voltage causes charge (i.e. current) to flow in a particular direction. Current, is the rate that charge passes through a medium. Moreover, charge delivered in coulombs is equal to the current level in amperes multiplied by the time in seconds (i.e. charge (C)=current (A)×time (s)). In a wire (or lead) current is carried by electrons. In extracellular fluid (such as in a tumor), current may be carried by an ion in solution.

Although electrical therapy examples described hereinbelow may be expressed in voltage (i.e. volts) and/or current (i.e. amperes), it should be understood that by applying Ohm's law, which states that voltage and current are proportional (i.e. V=IR), the equivalent voltage to current or current to voltage may be calculated. The proportionality constant is the resistance (R) in the electrode/tissue system. Resistance is measured in ohms ($\Omega$) and is equal to one volt per ampere. Resistance is the property of a material to resist current flow. In the electrical therapy system described herein, resistance may be caused by any number of factors including tumor density, tumor consistency, tumor volume, tumor location, pharmaceuticals utilized, wire(s) (or lead) utilized, electrode(s) utilized, and patient characteristics such as weight, age, gender, and diet. Because resistances may change with long-term electrical therapy, it may be advantageous to program the devices of the present embodiment in terms of current instead of voltage. For example, in DC ablation, if 10 mA are applied to a tumor with a resistance of 100Ω the corresponding voltage is 1 V. However, if 10 mA are applied to a tumor with a resistance of 25Ω the corresponding voltage is 0.25 V. In another example consistent with electroporation, if 500 V are applied to a tumor with a resistance of 25Ω the corresponding current is 20 A. However, if 500 V are applied to a tumor with a resistance of 100Ω the corresponding current is 5 A.

Electrical therapy may also be described as total coulombs (C) delivered. As will be appreciated by those of ordinary skill in the art, describing electrical therapy in terms of total coulombs (C) delivered can apply to numerous ranges of volts and amperes dependent on the resistance of the system and the rate of delivery. Therefore, because resistance may vary widely from one tumor to another, each of the examples of the preferred embodiments described herein are merely examples and are not limiting. In each situation resistance of a tumor may be measured prior to application of electrical therapy to determine the appropriate voltage, current, and/or coulombs to be delivered.

For example, if a dose of 0.5 C is applied to a tumor the resulting voltage and current varies dependent on the rate at which the charge is delivered and the resistance of the system. If, for example, the resistance of the system is 100Ω and the rate of delivery is for a period of 10 seconds then the resulting current is 0.05 A (50 mA) and the resulting voltage is 5 V. In some circumstances it may be advantageous to deliver the charge over a longer time period such as in DC ablation. For example, if a dose of 25 C is applied to a tumor over 1 hour and the resistance is 100Ω then the resulting current is 0.007 A (7 mA) and the resulting voltage is 0.7 V. In electroporation, electrical therapy is delivered over a short time period. For example, if 1 mC is applied to a tumor over 1 ms and the resistance is 1000Ω then the resulting voltage is 1000 V and the resulting current is 1 A.

With regard to the preferred methods of the embodiment, single electrode and/or multi-electrode configurations of the preferred embodiment may be used in conjunction with electrical therapy regimens.

In the case of a single electrode configuration, medium voltage may be applied for minutes to hours between a lead electrode and the generator housing, which generates a pH change of at least 2 in either direction to begin destruction of cancerous tissue. Following application of medium voltage, a rest period, marked by idling of the device, is optionally entered. Later, low voltage may be applied for hours to days, which may attract white blood cells to the tumor site. In this way, the cell mediated immune system may remove dead tumor cells and may develop antibodies against tumor cells. Furthermore, the stimulated immune system may attack borderline tumor cells and metastases. Molecular chlorine generated at the anode may kill additional local tumor cells.

Various adjuvants may be used to increase any immunological response, depending on the host species, including but not limited to Freund's adjuvant (complete and incomplete), mineral salts such as aluminum hydroxide or aluminum phosphate, various cytokines, surface active substances such as lysolecithin, pluronic polyols, polyanions, peptides, oil emulsions, and potentially useful human adjuvants such as BCG (bacille Calmette-Guerin) and Corynebacterium parvum. Alternatively, the immune response could be enhanced by combination and or coupling with molecules such as keyhole limpet hemocyanin, tetanus toxoid, diptheria toxoid, ovalbumin, cholera toxin or fragments thereof.

In the case of a multi-electrode configuration, medium voltage may be applied for minutes to hours between a first set of one or more electrodes and either a second set of one or more other electrodes, or the generator housing.

In any case, medium voltage may be applied for minutes to hours between at least one anode and at least one cathode.

Any number and configuration of electrodes comprising either anodes or cathodes, or anodes and cathodes may be used.

In some embodiments the generator housing serves as either an anode or a cathode.

As with the single electrode configuration, the medium voltage applied between at least one anode and at least one cathode generates a pH change of at least 2 in either direction to begin necrosis. Following application of high voltage, a rest period, marked by idling of the device, is optionally entered. Later, low voltage may be applied for hours to days, which may attract white blood cells to the tumor site. In this way, the cell mediated immune system may remove dead tumor cells and may develop antibodies against tumor cells. Furthermore, the stimulated immune system may attack borderline tumor cells and metastases.

As previously described, various adjuvants may be used to increase any immunological response.

Additionally, electrical therapy may be used in conjunction with chemotherapy and radiation therapy. Steps relating to single electrode and/or multi-electrode therapies may be followed by steps specifically designed for chemotherapy and radiation therapy.

In the case of electrical therapy used in conjunction with chemotherapy, at least one remote cathode may be implanted near a chemotherapy administration site or other site if the chemotherapy agent is administered systemically. Next, a chemotherapy agent is administered. Following administration of a (positively charged) chemotherapeutic agent, medium voltage is applied between at least one anode (e.g. the generator housing or first electrode coupled to the generator housing by a first lead) and at least one remote cathode (e.g. an electrode coupled to the generator by a lead or second electrode coupled to the generator by a second lead) to direct a chemotherapeutic agent to the tumor site. Alternatively, medium voltage may be applied between at least one cathode and at least one remote anode to direct a chemotherapeutic agent to the tumor site. Following the medium voltage step, the polarity of the generator housing (or first electrode) may switch with the polarity of the electrode (or second electrode) such that the generator housing (or first electrode) becomes cathodic and the electrode (or second electrode) becomes anodic. By reversing polarity of the generator housing (or first electrode) and electrode (or second electrode), the chemotherapeutic agent is dispersed throughout the peripheral tumor mass. Following polarity reversal, electroporation electrical therapy may be optionally administered to the tumor site in order to increase permeability of the cells to allow enhanced uptake of a chemotherapeutic agent. As is described hereinbelow, the devices and methods of the present embodiment may be adjusted for other variations, such as in the case of a negatively charged chemotherapy agent.

In the case of electrical therapy used in conjunction with radiation therapy, following the electrical therapy regimen as described for single electrode and/or multi-electrode configurations of the preferred embodiment, medium voltage is applied to all electrodes, thereby forcing all electrodes anodic, for minutes to generate molecular oxygen. Alternatively, various substances may be administered to oxygenate tissue, as described hereinbelow. In this embodiment, localized hyperoxia significantly increases brachytherapy effectiveness. As such, brachytherapy may be applied concomitantly to enhance the effects of electrical therapy.

Each of the previously described methods and method steps therein may be used in conjunction with each other for increased effectiveness. For example, chemotherapy and radiation therapy may be used in conjunction with the methods for unipolar and/or bipolar treatments.

Complexity of the device and therapeutic regimen can vary considerably, depending upon its desired flexibility of use. The device in its simplest form may consist of a single lead permanently connected to a generator encapsulated in plastic or potting compound (with an embedded generator housing electrode) with a fixed DC output voltage. Alternatively, a complicated device may have numerous options and configurations ideal for any particular situation. Examples of the numerous options and configurations suitable for implementing various embodiments are described in full detail hereinbelow. A therapeutic regimen in its simplest form may consist of a single voltage applied to a single electrode for an amount of time. However, many complicated therapeutic regimens are also contemplated. Examples of the types of complex therapeutic regimens suitable for implementing various embodiments are apparent in the following description.

The cancer therapy system of several embodiments differs from implantable pacemaker systems in various ways. For example, pacemakers (temporary pacemakers aside) are generally implanted for years while the device of such embodiments is typically implanted for hours to days or hours to months, until the cancerous condition has been ameliorated. The cancer therapy system described herein is not life-supporting as opposed to pacemakers, which are relied on by patients to stimulate their heartbeat. The generator housing of cancer therapy systems may have lower hermeticity requirements (i.e. higher leak rate tolerance) in comparison to hermeticity requirements of housings used with pacemaker generators because the device of the present embodiment is designed to be implanted for months not years. The leads of the present embodiment may have less stringent mechanical requirements since they are not stressed by movement (such as by the movement created by a beating heart) to the degree of pacemakers and are required for shorter periods of time, again months not years. Additionally, in most cases electromagnetic interference is not a concern with the cancer therapy system of the present embodiment as it is with pacemaker systems. However, electromagnetic interference may be a concern in the case of highly specialized systems wherein certain sensors are employed.

The cancer therapy device and methods described herein may advantageously utilize various imaging methodologies and apparatus for the purpose of tracking a patient's recovery. To this end, a medical practitioner may be interested in various types of data for the purposes of imaging and tracking a patient's progress. Examples of these types of data include current flow, pH change, temperature, and position. Examples of imaging available for this purpose include positron emission tomography (PET), computed tomography (CT), magnetic resonance imaging (MRI), and the like. Further discussion of imaging useful for use with the present embodiment may be found in related applications including U.S. Ser. No. 60/378,824 for "METHOD OF IMAGING BEFORE AND AFTER ELECTROCHEMICAL TREATMENT" filed May 9, 2002 and U.S. Ser. No. 10/434,400 for "METHOD AND DEVICE FOR TREATING CANCER IN CONJUNCTION WITH CHEMOTHERAPEUTIC AGENTS AND RADIATION THERAPY" filed May 7, 2003, which are hereby incorporated by reference.

In further embodiments, ambulatory adaptations of electrical therapy devices are described herein which advantageously increase versatility of electrical therapy systems. The ambulatory methods and devices herein may be used in conjunction with any of the practices taught in other applications and references cited herein. In one embodiment, an ambulatory device may comprise an implanted portion and an external portion. The implanted portion and the external portion may advantageously communicate by any communication means. Communication means may include, for example, hardwired connections and wireless connections. The two portions, implanted and external, may also be electrically coupled via a hardwire connection or wireless connection such that the two portions may each contribute power to the electrode or electrodes implanted into a patient for the treatment of cancer.

In another embodiment, a monitor for recording fluctuations in the device output and/or environmental or health status of a patient may be utilized (e.g. a Holter monitor). For example, the monitor may measure any of a patient's body temperature, heart rate, and pulse. The monitor may also measure impedance, voltage output, and current output. The monitor may also record results of PET, CT, and MRI scans, such as positioning data. In one embodiment, the implanted (or internal) portion may sense data which is then communicated to the external portion. After being received at the external portion, the data may be converted (i.e. formatted or compiled) into an oncogram. Further descriptions of oncograms may be found in U.S. Ser. No. 10/434,400 for "METHOD AND DEVICE FOR TREATING CANCER IN CONJUNCTION WITH CHEMOTHERAPEUTIC AGENTS AND RADIATION THERAPY" filed May 7, 2003, which is hereby incorporated by reference.

Referring now to the drawings, further features and embodiments are now described.

In FIGS. 1a and 1b, a partially implantable device 10 of the present embodiment for treating cancer is depicted. The partially implantable device 10 comprises a generator 1, one or more leads 3 and 4, and one or more electrodes 9 and 11. Also shown are a patient 5, skin incision 7, and tumor area 8.

In the present embodiment, two leads 3 and 4 are coupled at one end to the generator 1. In this example the generator 1 is worn externally to the patient 5. The generator 1 may be coupled to the leads 3 and 4 through a hardwire connection (e.g. through ports and/or docking means) or a wireless connection (e.g. via radio frequency and/or electromagnetic induction). In this case, the generator 1 is hardwired to the leads 3 and 4.

At the other end of the leads 3 and 4 (i.e. the distal end of leads) are electrodes 9 and 11. Depicted herein the electrodes 9 and 11 are placed in the tumor area 8. However, depending on certain variables and circumstances of the specific treatment regimen, the electrodes 9 and 11 may be placed in alternate locations within the patient 5. Examples of circumstances when alternate placement of one or more electrodes may be advantageous include when electrical therapy is used in combination with chemotherapy and/or radiation therapy. Additional information regarding the use of chemotherapy and/or radiation therapy in conjunction with electrical therapy may be found in U.S. Ser. No. 10/434,400 for "METHOD AND DEVICE FOR TREATING CANCER IN CONJUNCTION WITH CHEMOTHERAPEUTIC AGENTS AND RADIATION THERAPY" filed May 7, 2003 which is incorporated herein by reference.

The leads 3 and 4 pass through the skin incision 7. Therefore the leads 3 and 4 are partially implanted into the patient 5. The portion of leads 3 and 4 shown diagrammatically below skin incision 7 in FIG. 1a are implanted into the patient 5 whereas the portion of leads 3 and 4 shown diagrammatically above the skin incision 7 are external to the patient 5. In one embodiment, the generator 1 may be worn at a location external to the patient 5 near the location of the implanted electrodes 9 and 11, as shown in FIG. 1b.

Illustrated in FIGS. 2a, 2b, 2c, and 2d are additional examples of partially implantable devices 10. Shown are an external generator 20, lead 21, skin incision 22, tumor environment 23, indifferent electrode 24, instrument 25, pathway 26, conductor 27, internal generator portion 28, pod 29, and conductor 30.

Looking first at FIG. 2a, the external generator 20 is coupled to the lead 21. Also coupled to the external generator 20 is the indifferent electrode 24. The lead 21 passes through the skin incision 22 where it is implanted into a patient (not shown). As shown in the present embodiment, the lead 21 may be placed in the tumor environment 23. Although shown in FIG. 2a is a single lead 21, it should be understood that in other variations of the preferred embodiment, additional leads, in various configurations, may be utilized. Additionally, the lead 21 may have any number and configuration of electrodes (not shown). Numerous examples of lead configurations and electrode configurations useful with the present embodiment may be found in U.S. Ser. No. 10/434,400 for "METHOD AND DEVICE FOR TREATING CANCER IN CONJUNCTION WITH CHEMOTHERAPEUTIC AGENTS AND RADIATION THERAPY" filed May 7, 2003 which is incorporated herein by reference. In the case that two leads (not shown) are used with the external generator 20 at least one anode electrode (not shown) and one cathode electrode (not shown) may be implanted. In the case that two leads (not shown) with at least one anode electrode (not shown) and one cathode electrode (not shown) are implanted, the indifferent electrode 24 may or may not be included in external generator 20. If included, the indifferent electrode 24 may or may not be activated, as desired.

In certain variations of the present embodiment, the external generator 20 may be coupled to an instrument 25, as shown in FIG. 2a. The instrument 25 is located externally to a patient (not shown). The instrument 25 may communicate (or interact) with the generator 20 via pathway 26 which may be a hardwired connection or a wireless communication path. The generator 20 may be sealed to any degree desired and may be of any desired shape and size. Generator 20 may contain its own power source and electronics (e.g. circuitry, battery) necessary to perform the desired therapy or it may derive some (or all in some instances) of its power from instrument 25. In one embodiment, the generator 20 may have a backup battery for use when charging the device or during primary battery replacement. Generator 20 may also provide data to instrument 25 via path 26.

Shown in FIG. 2b, the external generator 20 is coupled to the lead 21. The lead 21 passes through the skin incision 22 where it is implanted into a patient (not shown). As shown in the present embodiment, the lead 21 may be placed in the tumor environment 23. Also coupled to the external generator 20 is the indifferent electrode 24. The indifferent electrode 24 is coupled to the generator 20 via the conductor 27. This configuration permits the indifferent electrode 24 to be located at a remote site on the body. Similarly to FIG. 2a, the external generator 20 may be coupled to the instrument 25.

Shown in FIG. 2c, the external generator 20 is coupled to the pod 29 by way of the conductor 30. The implanted generator portion 28 is coupled to a lead 21. The implanted generator portion 28 and lead 21 are implanted into the patient (not shown). The lead 21 may comprise any number and configuration of electrodes (not shown). Additionally, the implanted generator portion 28 may have any number of leads; one lead 21 is shown here for purposes of clarity. In the case, however, that a single electrode on lead 21 is utilized, the implanted generator portion 28 may serve as an electrode 24.

The external generator 20 interacts with the implanted generator portion 28 by an interacting means. As shown, the external generator 20 interacts with the implanted generator portion 28 by way of the pod 29. Interaction between the external portion 20 and the implanted portion 28 may be to control the implantable portion (i.e. direct the function of the implantable portion), provide power to the implantable portion, monitor the implantable portion, and received data from the implantable portion. Communication between the pod 29 and the implanted generator portion 28 may be by any means including, for example, radio frequency and electromagnetic induction. The pod 29 may be used solely for charging implantable generator portion 28, which may contain all or part of the other electronics in the generator system.

This configuration including a wholly implanted lead 21 and implanted generator portion 28 with an external generator portion 20 advantageously reduces risk of infection and/or lead dislodgement that is inherent in other embodiments, such as the partially implanted configurations of FIGS. 2a and 2b. The skin incision 22 of FIG. 2c is initially performed by a medical practitioner who implants the lead 21 and the implanted generator portion 28; however, the skin incision 22 eventually heals by way of the patient's own healing processes. Similarly to FIG. 2a, the external generator 20 may be coupled to the instrument 25.

The partially implanted configurations of FIGS. 2a and 2b may permit locating the generator 20 farther from the tumor environment 23 and may be desirable in an environment of ionizing radiation which could damage or interfere with the performance of the electronics within the generator 20. However, in one embodiment of the present embodiment of FIG. 2c, the pod 29 and/or implanted generator portion 28 may contain materials that are resistant to ionizing radiation. Alternatively, the pod 29 and/or implantable generator portion 28 may be designed such that components that are susceptible to damage by ionizing radiation are excluded from any pod 29 and/or implantable generator portion 28.

Additionally, in the case of the partially implanted configurations described herein, an internal (or implantable) portion may include a first power supply and an external portion may include a second power supply. A second power supply may, for example, provide any or all of electrolysis, DC ablation, electroporation, and electrochemical therapy.

Similarly to FIG. 2c, the device of FIG. 2d comprises the wholly implantable generator portion 28 which is coupled to the wholly implanted lead 21. The implanted lead 21 terminates at the distal end with at least one electrode (not shown). As with FIG. 2c, the skin incision 22 is made by a medical practitioner when the implantable device (consisting of the implantable generator portion 28 and lead 21) is implanted into the patient (not shown). The skin incision 22 eventually heals after implantation.

Unlike the device of FIG. 2c, the device of FIG. 2d does not incorporate a pod (not shown). In this embodiment, the external generator 20 communicates directly with the implantable generator portion 28. The external generator 20 may be used solely for charging implantable generator portion 28, which may contain all or part of the other electronics (e.g. circuitry, battery) in the generator system. The external generator 20 may communicate with the implantable generator portion 28 by any means including those referenced hereinabove. The external generator 20 may be coupled to the instrument 25 as described hereinabove in FIG. 2a.

Figure 4:
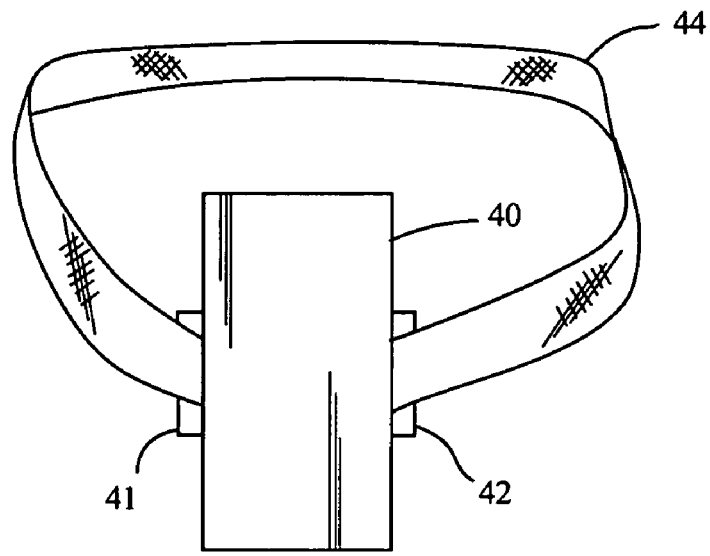
FIG. 4 is an illustration of the external generator of FIG. 3 with the addition of strap coupled thereto.

Turning now to FIGS. 3 and 4, an external generator 40 suitable for use with any of FIGS. 1 and 2a-2d is depicted. Shown are the external generator 40, loops 41 and 42, and strap 44. The generator 40 is designed for easy attachment to an object, such as a patient's body, by way of loops 41 and 42. The generator 40 may be attached (or affixed) to any suitable part of a patient's body, such as, for example, around an arm, around a leg, around the waist, and at the hip. As shown in FIG. 3, the loops 41 and 42 are placed on either side of the external generator 40. It should be understood, however, that any number of loops in any configuration and location may be utilized with the present embodiment. Additionally, any other type of affixing means may be utilized to secure the external generator 40 to a patient. Examples of affixing means include strapping, snapping, tying, and "velcroing" the external portion to the object.

In the present configuration, a strap 44 may pass through the loops 41 and 42 located at either side of the external generator 40 as shown in FIG. 4. The strap 44 may be of any material suitable for affixing the generator 40 package securely to a patient's body. For example, the strap 44 may be made out of cloth or plastic and may feature closure mechanisms such as snaps, buckles, or Velcro®. The generator package 40 may be located outside of the patient's clothing on an area of the body distant from the tumor (not shown) and/or implanted lead or leads. In another embodiment, the strap may be secured to an item beside the patient's body such as an IV bracket, a bed, or even a location farther away from the patient. Furthermore, the generator 40 may be attached to the patient, IV bracket, or bed by means other than loops 41 and 42 such as snaps or Velcro®.

In a preferred embodiment, the external generators described herein (such as in FIG. 1, FIG. 2a-2d, FIG. 3, and FIG. 4 hereinabove) are resistant to environmental hazards such as liquids, dropping from heights, and being crushed. Low cost and weight may also be desired, but often the usefulness of these features is a trade-off between cost, ease of use, and versatility. The appropriate level of protection may vary depending on the specifics of any particular case. In one example, if an electrode 24 such as the electrode shown in FIG. 2a is used, the generator 20 must make good electrical contact with the skin adjacent the electrode. In another example, if the electrode 24 of FIG. 2b is used, only the electrode 24 must make good contact with the skin.

Figure 5:
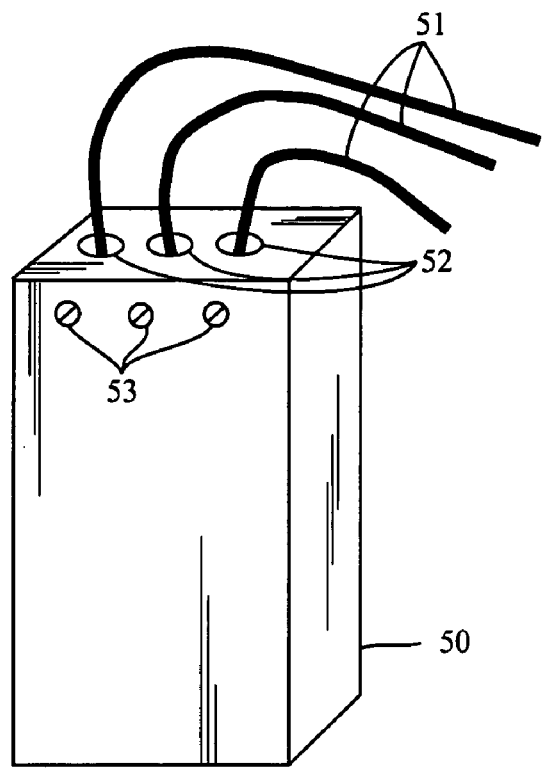
FIG. 5 is a drawing of an external generator to which one or more leads are attached.

Depicted in FIG. 5 is an external generator 50 to which one or more leads 51 are attached. Shown are the generator 50, the leads 51, connectors 52, and screws 53. The proximal ends of leads 51 make electrical and mechanical contact with connectors 52. The proximal end of the leads 51 are secured to the generator 50 by attaching means. As shown herein, attaching means are the screws 53. However, attaching means may be any of a variety of attachments appropriate for lead fixation including clips, thumbscrews, collets, plugs, and the like. The screws 53, in this case, retain leads 51 and cause electrical contact to be maintained with their proximal ends as the leads 51 are electrically insulated except for the proximal ends at connectors 52. The leads 51 of FIG. 5 are individually insulated, such that each lead 51 is electrically separated from the other leads 51.

In general, power may be supplied by only the generator 50, by another instrument (not shown), or by the generator 50 in conjunction with another instrument (not shown). In either case, however, the power is distributed from the generator 50 to the leads 51 which is then supplied to electrodes (not shown). Although three leads 51 are shown in the present embodiment, it should be understood that any number of leads and electrodes in any configuration may be utilized.

Figure 6:
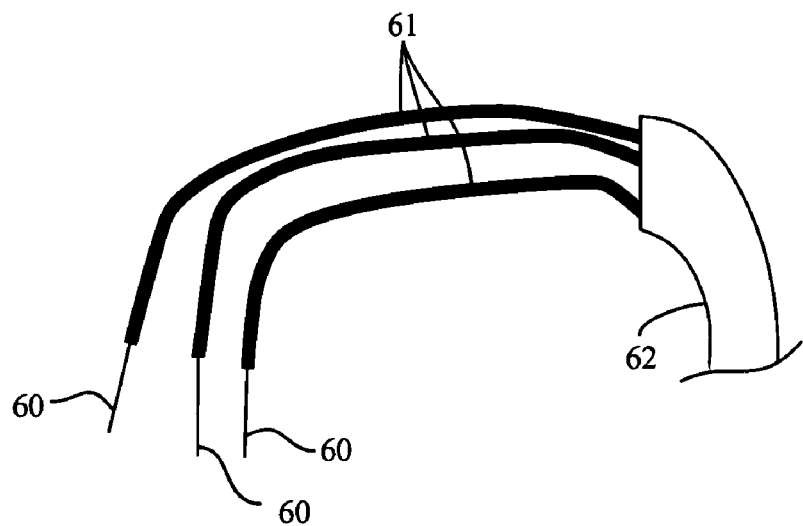
FIG. 6 is a depiction of a lead bundle for use with a generator, such as the generator of FIG. 5.

The leads of FIG. 6 are bundled as may be advantageous in various situations. Shown are proximal uninsulated ends 60, insulated leads 61, and outer covering 62. The proximal uninsulated ends 60 of insulated leads 61 are uninsulated for purposes of making electrical connections. For example, the uninsulated proximal ends 60 of FIG. 6 may be inserted into the connections 52 of FIG. 5. The insulated leads 61 are shown inserted into an outer covering 62. The outer cover 62 may be useful to hold the lead bundle together and to add strength to the lead bundle.

The added strength that the outer covering 62 lends to the lead bundle is especially advantageous in the case of a bundle external to a patient's body because external lead portions are generally susceptible to stresses greater than those within the body. The stresses associated with the external lead bundles of the present embodiment are similar to the stresses made on external pacemaker leads. However, the portion of the lead within the body is generally exposed to less stress than in permanent implantable pacemaker leads.

Shown in FIGS. 7a and 7b are lead designs useful with the present embodiment. Shown are a first lead 300, tumor environment 301, under body surface 302, a second lead 303, and a point of connection 304. Turning first to FIG. 7a, the first lead 300 is coupled to the second lead 303. The first lead 300 penetrates the body surface 302. At the point of connection 304, the first lead 300 and second lead 303 mate to form a connection. For example, the first lead 300, which is preferably a reusable lead comprised of a heavy, sturdy material has a connector (not shown) that corresponds to a mating connector on the second lead 303. The second lead 303 is implanted below the skin surface 302 and its distal end is within the tumor environment 301. The first lead 300 loses sterility after the implantation procedure.

FIG. 7b is a variation of FIG. 7a comprising an implanted generator 305. If for any reason during treatment, it is desired to use the implanted generator 305, the design of FIG. 7a can be modified to accommodate such a device. As shown in FIG. 7b, the generator (or a portion thereof) 305 is implanted below the skin surface 302 and mated to lead 303 using the connector at the point of connection 304 as described hereinabove. Both of the designs of FIGS. 7a and 7b work to maintain lead strength outside of a patient's body while maintaining sterility for the implanted components.

In a preferred embodiment, the proximal tip of each lead described hereinabove may be designed similarly to a pacemaker lead tip and may contain two or more electrodes arranged in an inline configuration, such as a proximal pin electrode and one or more ring electrodes inline with the proximal pin electrode.

FIG. 8 is an illustration of a fixation means useful for use with the present embodiment. Shown are a lead 70, a post 71, a cylindrical hole 72, lead tip 73, a cap 74, and a generator 75. The lead tip 73 of the lead 70 is threaded through the hole 72. The cap 74 works to secure the lead tip 73 to the generator 75 in conjunction with the post 71. The post 71 may be threaded so that the cap 74 can be screwed down and tightened to hold the lead tip 73 securely in place. The lead tip 73 and the post 71 are made of conducting material such that energy supplied by the generator 75 is conducted through the post 71 to the lead tip 73 and subsequently through the lead 70. The distal end of lead 70 may terminate in one or more electrodes (not shown). Although the post 71 and cap 74 securing mechanism is described in this example, it should be understood that numerous other connecting means and mechanisms may be employed.

Figure 9:
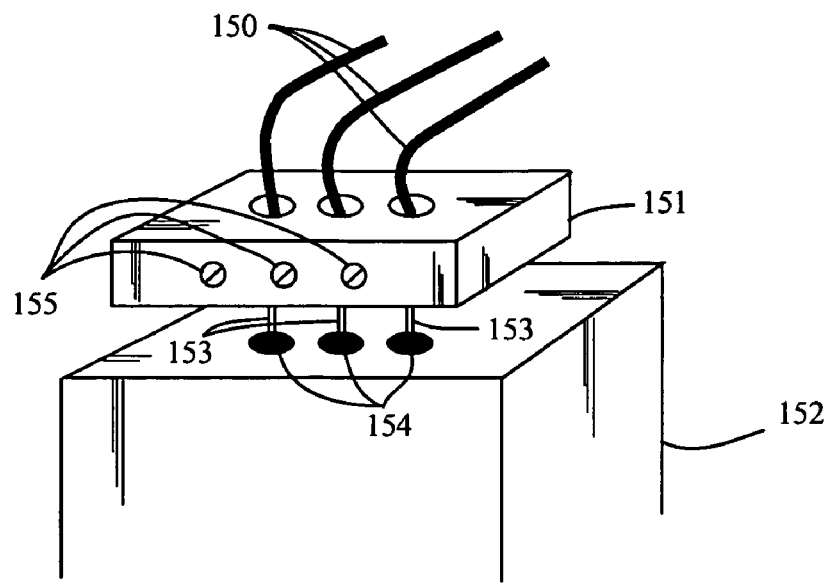
FIG. 9 is an illustration of a means for quick connection to and removal of leads from an external generator.

Illustrated in FIG. 9 is a means for quick connection to and removal of all leads 150 from an external generator 152. Shown are the leads 150, a block 151, the generator 152, pins 153, connectors 154, and screws 155. The leads 150 are coupled to block 151 by any means. However, in a preferred embodiment, the leads 150 may be coupled to the block via screws 155 such as described hereinabove in FIG. 5. The pins 153 electrically couple the leads 150 to the generator 152 via the connectors 154 into which the pins 153 plug. The connector block 151 may also have further means to hold it securely into position and may be keyed to prevent incorrect connection to the generator 152. The quick connection means described herein may be advantageous in numerous situations. For example, the quick connection may be useful when a patient bathes or when a patient undergoes radiation therapy. Other types of quick connects are envisioned, the quick connect described herein is one example of quick connects that may be used in the present embodiment.

Figure 10:
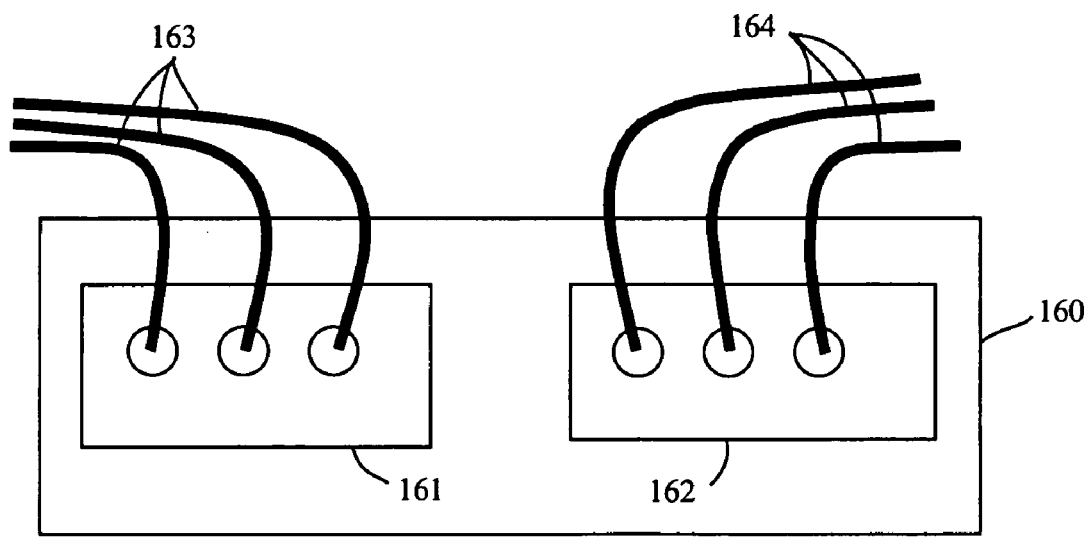
FIG. 10 is a drawing of a device useful for treating multiple tumors with a single generator.

Turning now to FIG. 10, a device useful for treating multiple tumors with a single generator is depicted. Shown are the top of a generator 160, a first connector block 161, a second connector block 162, a first set of leads 163, and a second set of leads 164. The first connector block 161 and the second connector block 162 are electrically coupled to the top of the generator 160. As shown herein, the first connector block 161 and the second connector block 162 are coupled by plugging means. The first set of leads 163 are coupled to the first connector block 161 and the second set of leads 164 are coupled to the second connector block 162. The distal ends of the first set of leads 163 are implanted near or in a first tumor environment (not shown) while the distal ends of the second set of leads 164 are implanted near or in a second tumor environment (not shown). The distal ends of the first set of leads 163 and the distal ends of the second set of leads 164 may terminate in any number and configuration of electrodes.

The multiple connector blocks 161 and 162 of the present embodiment are especially useful in situations where a patient has multiple tumors and/or a very large tumor. Patients often have primary tumors and metastases and it is therefore advantageous to implant electrodes in each of several tumors in order to apply therapy simultaneously. Using the device of FIG. 10, a single generator 160 may supply power to multiple sets of leads 163 and 164. Although two connector blocks 161 and 162 with three leads each are shown in FIG. 10, it should be understood that any number of connector blocks and any number of leads can be employed with the present embodiment.

Figure 11:
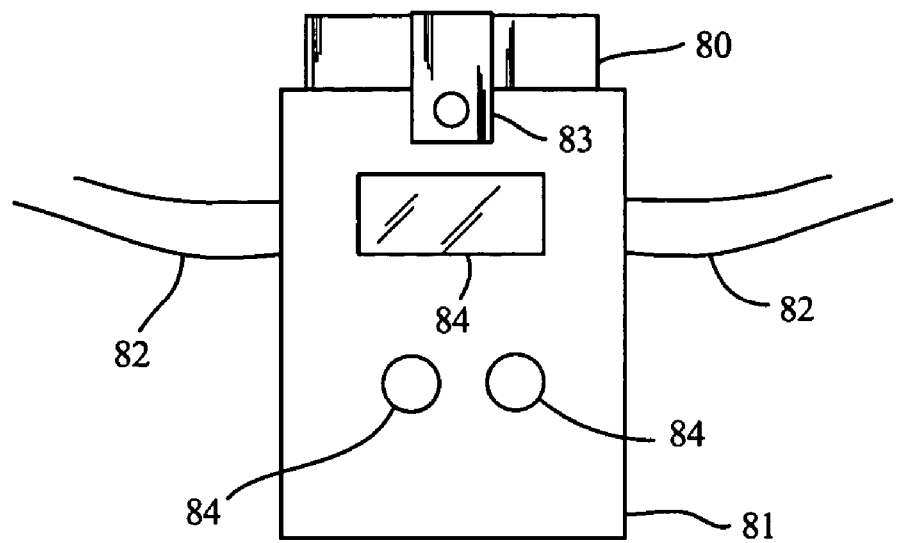
FIG. 11 is a depiction of an external generator contained in a protective pouch.

Illustrated in FIG. 11 is an external generator 80 contained in a protective pouch 81. Although shown herein as a pouch 81, any type of external portion containing apparatus is envisioned. Shown are the external generator 80, a pouch (or external portion containing apparatus) 81, straps 82, snap 83, and openings 84. The pouch 81 comprises straps 82 or other means to affix the generator assembly to a patient's body. The pouch 81 is useful for holding and protecting the generator 80 which is inserted into the pouch 81. Additionally, the pouch 81 may be designed to protect against tampering. For example, the pouch 81 may comprise a securing device, such as the snap 83 for securing the generator 80 into the pouch 81. The pouch 81 may also comprise openings 84 which only allow certain controls to be accessed or certain displays to be seen. Although not shown, leads may extend from the top of the generator 80 which is shown protruding from the top of the pouch 81. The leads (not shown) terminate in any number and configuration of electrodes (not shown) which are strategically placed in or on the patient's body depending on the particular case. Numerous examples of lead placement can be found in U.S. Ser. No. 10/434,400 for "METHOD AND DEVICE FOR TREATING CANCER IN CONJUNCTION WITH CHEMOTHERAPEUTIC AGENTS AND RADIATION THERAPY" filed May 7, 2003 which is incorporated herein by reference. In a further embodiment, the generator 80 may also serve as an electrode. In the case that the generator 80 serves as an electrode, the pouch 81 would have an opening on the side adjacent to the patient's body such that electrical contact is made between the patient's skin and the electrode on the generator 80.

In another embodiment, the pouch 81 may contain additional shielding to protect the generator 80 from electromagnetic interference or damage by ionizing radiation. The pouch 81 may be designed to be disposable and/or sterilizable. In yet another embodiment, the pouch 81 may be waterproof to allow, for example the patient to bath while wearing the generator 80. The pouch 81 of the present embodiment may comprise any number of variations including shape, size, material, shielding, security devices, affixing means, and the like.

Figure 12:
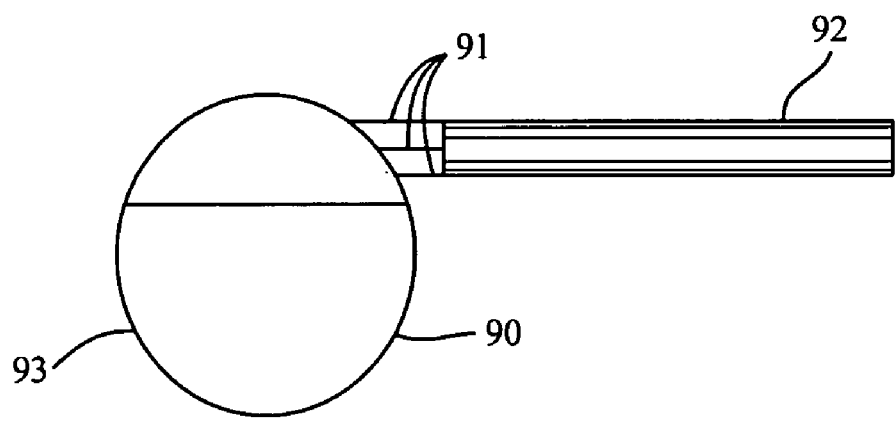
FIG. 12 is an illustration of an implantable generator having three leads encapsulated in a bundle.

Shown in FIG. 12 is an implantable generator 90 having three leads 91 encapsulated in a bundle 92. Shown are the implantable generator 90, the leads 91, the bundle 92, and an embedded electrode 93. Three leads 91 are coupled to the implantable generator 90. In a preferred embodiment, the leads 91 may be inserted into a bundle 93. Although three leads 91 are shown in the present embodiment, it should be understood that any number of leads may be used. Furthermore, although a single bundle 92 is depicted, it should be understood that any number of bundles may be utilized. For example, in the case of multiple tumors being treated with the same generator 90, several bundles 92 containing various numbers of leads may be employed.

The leads 92 terminate at the distal end with any number and configuration of electrodes (not shown). In another embodiment, the embedded electrode 93 may be utilized. The implantable generator 90 of the present embodiment does not have external mechanical controls (such as the external generator 80 of FIG. 11). The implantable generator 90 may, however, communicate over a wireless connection to a transmitter/receiver via radio, electromagnetic induction, and/or sound.

Figure 13:
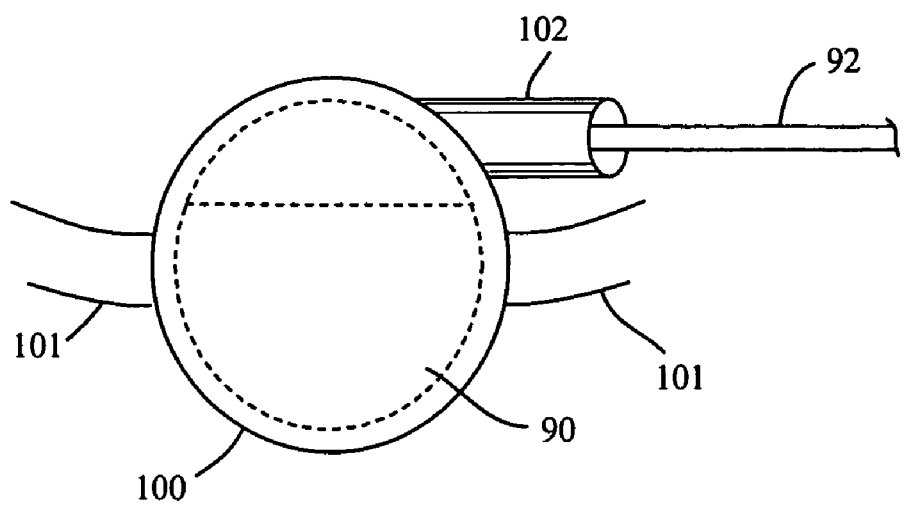
FIG. 13 is a drawing of an external version of the generator of FIG. 12.

Depicted in FIG. 13 is an external version of the generator 90 of FIG. 12. Shown in FIG. 13 are the generator 90, the lead bundle 92, a pouch 100, straps 101, and shield 102. The generator 90 of FIG. 13 is not implanted as in FIG. 12; rather, the generator 90 of FIG. 13 is encapsulated by the pouch 100 which may be worn externally to the patient. Straps 101 may be used for attachment of the generator 90 package to the patient's body or some other location. Similarly to the implanted generator 90 of FIG. 12, however, a lead bundle 92 protrudes from the generator 90. The lead bundle 92 contains one or more leads (not shown) which direct electrical therapy to a cancerous tumor (not shown).

The shield 102 protrudes from the pouch 100 to protect and secure the lead bundle 92. Specifically, the shield 102 may be useful for preventing fracture of the individual leads (not shown). The shield 102 may be coupled to the generator 90 directly or to the pouch 100.

A primary battery-powered implantable generator will be designed with a low quiescent current drain because its batteries are not replaceable. A rechargeable battery-powered implantable generator will also benefit from a low quiescent current drain so that the need for recharging it will be infrequent. An external generator will also benefit from a low quiescent current drain but can be designed with a higher one than the implantable device in order to save money or because it must support the drain of displays and control mechanisms. Typical battery capacities for alkaline non-rechargeable AA cells and 9 volt cells are 1700 mA-hr and 500 mA-hr, respectively. AA rechargeable cells are available with a capacity of 2000 mA-hr. Although the external generator may be designed to use many different battery types, hospitals may prefer to use standard batteries such as those mentioned above that are stocked for other hospital purposes. Assuming negligible quiescent current drain, the table below shows some examples of the various therapies possible using batteries of the above types.

| Battery Capacity | Therapy |
| --- | --- |
| 500 mA-hrs | Apply 50 mA in two 5-hour sessions |
| | Apply 25 mA in five 4-hour sessions |
| 1700 mA-hrs | Apply 50 mA in six 5-hour sessions |
| | Apply 25 mA in seventeen 4-hour sessions |
| 2000 mA-hrs | Apply 50 mA in eight 5-hour sessions |
| | Apply 25 mA in twenty 4-hour sessions |

A hospital or clinic may choose to replace or recharge the batteries for each new patient.

Figure 14:
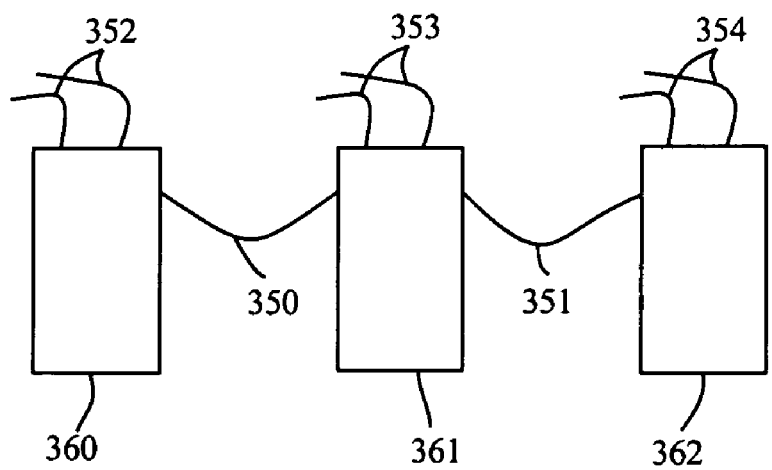
FIG. 14 is an illustration of a device useful for treating multiple tumors and/or expanding the number of electrodes powered by a single generator.

The device of FIG. 14 is useful for treating multiple tumors and/or expanding the number of electrodes powered by a single generator. Shown are a first generator 360, a second generator 361, a third generator 362, a first cable 350, a second cable 351, a first set of leads 352, a second set of leads 353, and a third set of leads 354. As shown in FIG. 14, the three generators 360, 361, and 362 are interconnected by way of the interconnection cables 350 and 351. The first interconnection cable 350 couples the first generator 360 to the second generator 361. The second interconnection cable 351 couples the second generator 361 to the third generator 362, such that all three generators 360, 361, and 362 are coupled together. The first generator 360 comprises a first set of leads 352, the second generator 361 comprises a second set of leads 353, and the third generator 362 comprises a third set of leads 354.

Each generator 360, 361, and 362 may independently treat one tumor (not shown). Alternatively, through the use of interconnection cables 350 and 351 the generators 360, 361, and 362 may work together to treat multiple tumors simultaneously. Specifically, the generators 360, 361, and 362 are capable of recognizing a daisy chained configuration and can, therefore, synchronize the operation of all of the generators 360, 361, and 362. In one embodiment, the first set of leads 352 coupled to the first generator 360 may be used to treat a first tumor (not shown) while the second set of leads 353 coupled to the second generator 361 simultaneously treat a second tumor (not shown) and the third set of leads 354 coupled to the third generator 362 simultaneously treat a third tumor (not shown). In yet another embodiment, a large tumor (not shown) may be treated by electrical therapy provided by the first set of leads 352 and the second set of leads 353 which are coupled to the first generator 360 and the second generator 361, respectively, while a second tumor (not shown) is being treated by the third set of leads 354 which is coupled to the third generator 362.

Figure 15:
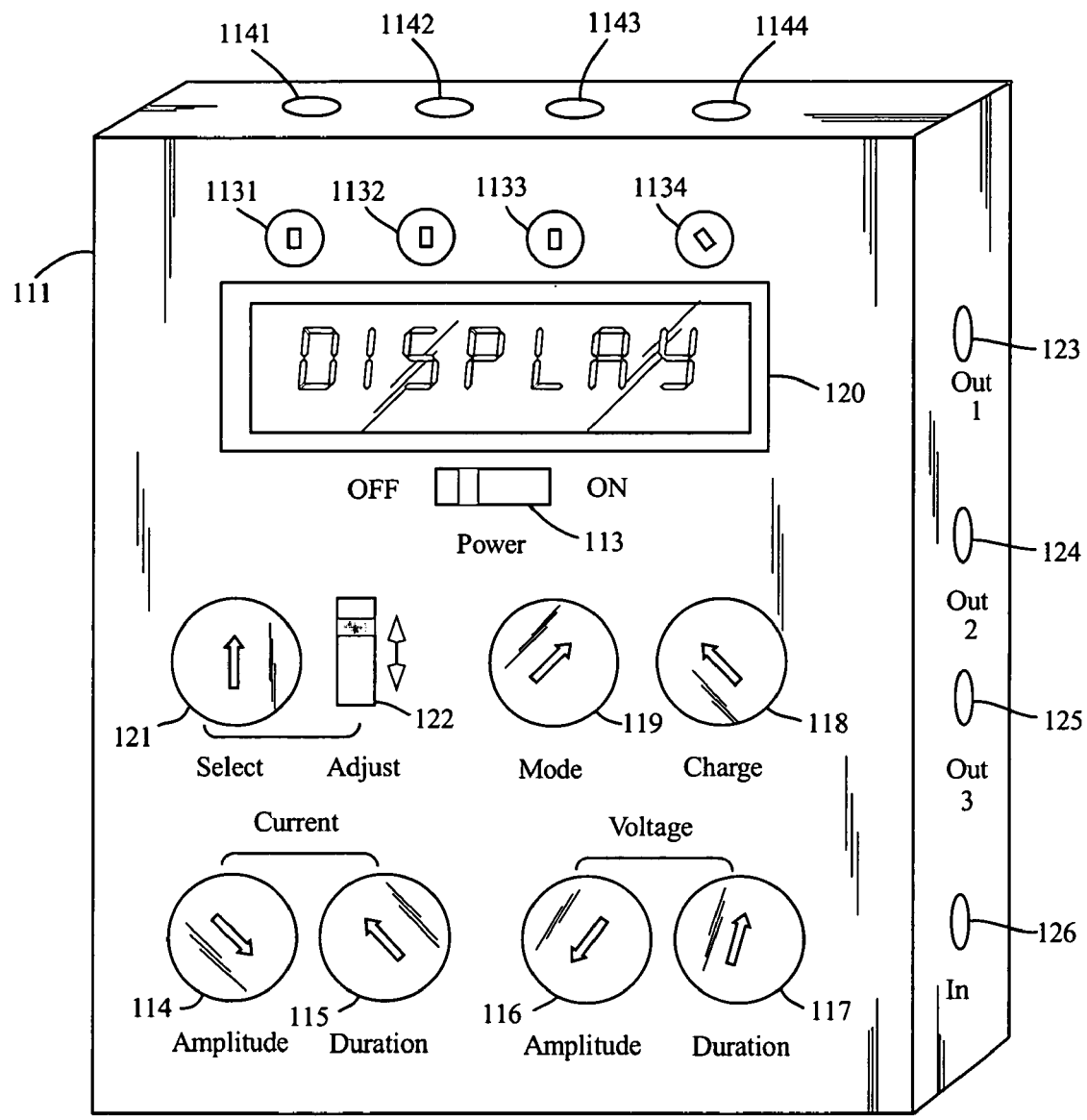
FIG. 15 is a representation of an external generator for use with the electrical therapy system of the preferred embodiment.

FIG. 15 is a representation of an external generator for use with the electrical therapy system of the preferred embodiment. Shown are the external generator 111, current amplitude output control 114, current duration output control 115, voltage amplitude output control 116, voltage duration output control 117, charge control 118, mode control 119, display 120, control 121, switch 122, first output connector 123, second output connector 124, third output connector 125, input connector 126, first electrode control 1131, second electrode control 1132, third electrode control 1133, fourth electrode control 1134, first lead connector 1141, second lead connector 1142, third lead connector 1143, and fourth lead connector 1144.

Lead connectors 1141, 1142, 1143, and 1144 are located on the top of the external generator 111. On the front panel of the external generator 111 are electrode controls 1131, 1132, 1133, and 1134. The first electrode control 1131 is coupled with the first lead connector 1141 such that the polarity (i.e. anode or cathode) of an electrode (not shown) coupled to the generator 111 by way of a lead (not shown) is controlled by the first electrode control 1131. Alternatively, the first electrode control 1131 may be set such that the electrode (not shown) coupled thereto is turned off. The second electrode control 1132 is coupled with the second lead connector 1142 such that the polarity (i.e. anode or cathode) of an electrode (not shown) coupled to the generator 111 by way of a lead (not shown) is controlled by the second electrode control 1132. Alternatively, the second electrode control 1132 may be set such that the electrode (not shown) coupled thereto is turned off. The third electrode control 1133 is coupled with the third lead connector 1143 such that the polarity (i.e. anode or cathode) of an electrode (not shown) coupled to the generator 111 by way of a lead (not shown) is controlled by the third electrode control 1133. Alternatively, the third electrode control 1133 may be set such that the electrode (not shown) coupled thereto is turned off. The fourth electrode control 1134 is coupled with the fourth lead connector 1144 such that the polarity (i.e. anode or cathode) of an electrode (not shown) coupled to the generator 111 by way of a lead (not shown) is controlled by the fourth electrode control 1134. Alternatively, the fourth electrode control 1134 may be set such that the electrode (not shown) coupled thereto is turned off. Although four lead connectors 1141, 1142, 1143, and 1144 and four electrode controls 1131, 1132, 1133, and 1134 coupled thereto (respectively) are described herein, it should be understood that any number of lead connectors and electrode controls may be utilized. Furthermore, it is not necessary that the number of lead connectors equal the number of electrode controls. For example, more than one lead connector may be coupled to a single electrode control.

The generator 111 may also comprise numerous other features such as a power control 113 for turning the supply of power to the generator on and off. Other controls may adjust output current amplitude 114 and output current duration 115 and/or output voltage amplitude 116 and output voltage duration 117. Alternatively, constant currents or constant voltages may be used in conjunction with the preferred embodiment. Charge to be delivered may be set via the charge control 118. Various standard stimulation modes can be chosen via the mode control 119. For example, the generator may apply a given amplitude of direct current for a given amount of time and then apply a different amplitude for another amount of time. As another example, the generator may automatically ramp up the current gradually to the selected final value. Another would be applying the current for a specific amount of time and then automatically shutting it off. The generator 111 may be designed to treat multiple tumors, with provisions for many leads and the selection of parameters for each tumor. In another embodiment, the generator 111 has a display 120 which may be a simple light display or a more sophisticated display such as an LCD screen. Using an alphanumeric display, parameters can be selected via the control 121 and adjusted to various values via the switch or potentiometer 122 while viewing the display 120.

Information obtained from the leads (not shown) may also be displayed, such as, for example, sensed electrode impedance. In yet another embodiment, one or more of the lead connectors 1141, 1142, 1143, and/or 1144 may receive sensor derived data from the tumor environment. In the case that the lead connectors 1141, 1142, 1143, and/or 1144 received sensor derived data, the appropriate electrode control (or controls) 1131, 1132, 1133, and/or 1134 are switched to recognize sensor data rather than electrode polarity. Calculated information from the data received can also be displayed as waveforms on, for example, the display screen 120. A practitioner may use the display 120 to preview an entire therapy session before activating the patient. Other parameters that can be set are the ramp-up characteristic of the current and voltage, the maximum current or voltage to be delivered, and activation of any warning signals. Warning signals may include low battery and lead dislodgement alerts. The warning signals may be audible or may be transmitted to a remote receiver to alert medical personnel. An automatic impedance monitor may be used to detect dislodgement. In another embodiment, battery status may be displayed.

On the side of the generator 111 are the first output connector 123, the second output connector 124, the third output connector 125, and the input connector 126. One or more of the output connectors 123, 124, and 125 may be used to send information to another device such as a printer, a computer, and/or a transmitter. Additionally, one or more of the output connectors 123, 124, and 125 may be used to interconnect generators via cables (such as the interconnection cables of FIG. 14). The input connector 126 may be used to feed in stimulus signals from another instrument.

A portion of the control panel of the generator 111 may be for patient use. For example, the patient may have control over output and drug flow should the electrical therapy become too painful, or for any other reason.

The generator 111 of FIG. 15 can comprise many different forms depending on the particular situation and patient needs. The numerous components and variations described herein can be used in any combination and configuration. The types of control mechanisms and functions shown in FIG. 15 are for illustrative purposes and may not represent the full range of possible designs. For example, controls may also include a keyboard and the generator may include an internal or external antenna. The external generator 111 may also have a compartment or a bracket for holding excess lead length. In another embodiment, the generator 111 may have a connector for a cable from an external power supply. An ambulatory (portable) external generator may weight in a preferred embodiment 10 to 200 grams, but 20 to 800 grams would also be acceptable. Leads for use with the present embodiment can be of any lengths but may typically range from 30 to 100 cm in length. The external generator may have battery conserving features, such as a display that turns off automatically when not in use.

Turning now to FIGS. 16a and 16b, an external generator 260 with a removable section 261 is shown. Shown are the generator 260, the removable section 261, jacks 262, and leads 265. FIG. 16a is a representation of the generator 260 with the removable section 261 inserted. FIG. 16b is a representation of the generator 260 without the removable section 261.

The removable section 261 may plug into the generator 260 by way of jacks 262. The leads 265 are coupled to the top of the generator 260. The removable section 261 may house sensitive components and/or components used to modify certain settings on the generator 260. The removable section 261 may be useful to eliminate access to the patient or others who might accidentally or intentionally modify settings. Additionally, the use of a removable section 261 will lighten the device when the section 261 is removed and to protect sensitive portions of the generator 260 when the device may be exposed to water, radiation, or other potentially harmful material. In another embodiment, the generator 260 may be able to accept various types of removable sections 261 such that more or less sophisticated plug-in sections (not shown) may be utilized in conjunction with the generator 260. For example, the external generator 260 may be used in a hospital setting with patients who need special capabilities or controls. The removable section 261 may differ in controls, energy source characteristics (such as capacity), and electronics. Another purpose of the removable section 261 is to update the external generator 260 as product improvements become available. Other reasons to remove section 261 are to calibrate and/or to recharge the section 261. The removable section 261 may be of any size and shape; in one example, the section 261 may be flat such as in a touch keyboard. Other devices, such as another instrument (not shown) may also be plugged into jacks 262 (or other connection means) for various purposes.

Depicted in FIG. 17 is an external generator 270 having an input connector 271. Shown are the generator 270, the input connector 271, instrument 272, cable 273, electroporation pulses 274, pulses 275, and leads 276. The instrument 272 is coupled via cable 273 to input connector 271 of the generator 270. The instrument is assumed to have capabilities that exceed those built into the external generator 270. For example, instrument 272 may be able to generate large electroporation pulses 274. In this case, the electroporation pulses 274 are generated in the instrument 272 and fed to the external generator 270 where the electroporation pulses 274 may or may not be modified into alternate pulses 275 and fed out leads 276 to the tumor environment.

In a further embodiment, instrument 272 may infuse a drug via a catheter (not shown) into the external generator 270 which controls the release of a drug through another catheter inserted into the patient's body. Electroporation (high voltage) pulses 274 may be used advantageously in conjunction with a chemotherapeutic agent. In yet another embodiment, a drug reservoir (not shown) may be implanted into a patient, where the drug reservoir may disperse a drug via an internal catheter (not shown) according to the provided electrical therapy regimen. The drug reservoir (not shown) may communicate with the generator 270 via hardwired or wireless communication as described hereinabove. Additional information regarding drug reservoirs, therapy regimens for use with chemotherapeutics (and radiation therapy), communication pathways between a generator and drug reservoir, and catheters may be found in U.S. Ser. No. 10/434,400 for "METHOD AND DEVICE FOR TREATING CANCER IN CONJUNCTION WITH CHEMOTHERAPEUTIC AGENTS AND RADIATION THERAPY" filed May 7, 2003 which is incorporated herein by reference.

Figure 18:
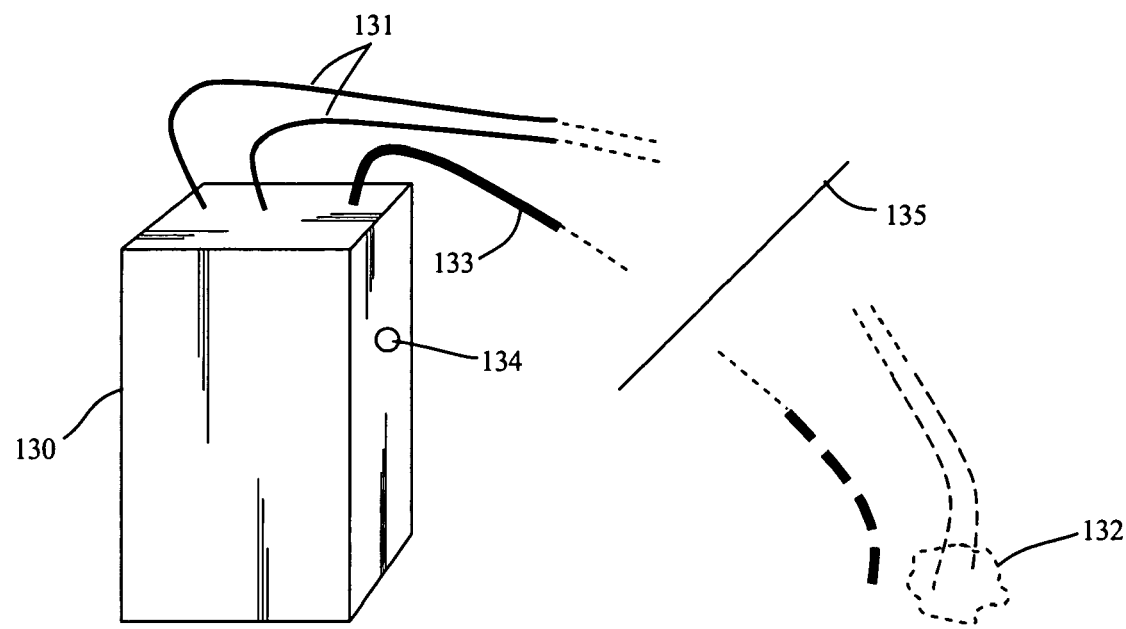
FIG. 18 is an illustration of a generator useful for distributing therapeutic agents.

Depicted in FIG. 18 is a generator 130 useful for distributing therapeutic agents. Shown are the generator 130, leads 131, a tumor 132, a catheter 133, a port 134, and body surface 135. The generator 130 is coupled to the leads 131 and the catheter 133. The distal ends of leads 131 may be implanted in or near a tumor 132 depending on the electrical therapy and/or chemotherapy regimen specified. The distal end of the catheter 133 is implanted in or near a tumor or, alternatively, in a blood vessel. The catheter 133 may contain a distal electrode and conductor so that it may also function as an electrical lead.

The generator 130 provides power to the leads 131 such that the electrodes at the end of the leads 131 are energized for the purpose of providing electrical therapy to a tumor or tumors. The generator 130 contains a drug reservoir (not shown) which contains one or more therapeutic agents. Examples of therapeutic agents include chemotherapy agents, pain control agents, adjuvants, and/or immunoenhancers. The drug reservoir (not shown) may be filled with a therapeutic agent by way of the filling port 134. From the drug reservoir (not shown) the therapeutic agent is pumped into the catheter 133. The therapeutic agent is eventually distributed to tissue located at the distal end of the catheter 133. Drug timing and dosage are controlled by the generator 130 according to, for example, the schedule programmed by the practitioner.

In another embodiment, the external generator 130 may be designed without drug infusion capabilities but can work in conjunction with a drug infusion pump that is either implanted or external. Communications between the devices can be designed according to the techniques disclosed in U.S. Ser. No. 10/434,400 for "METHOD AND DEVICE FOR TREATING CANCER IN CONJUNCTION WITH CHEMOTHERAPEUTIC AGENTS AND RADIATION THERAPY" filed May 7, 2003 which is incorporated herein by reference.

In any case, the generator 130 or drug infusion device may have a circadian rhythm monitor to optimize delivery of electrical and drug therapy. Monitoring may be accomplished by way of a timer, posture/activity detector (e.g. accelerometer, simple tilt switch, and/or gyroscope). The circadian rhythm monitor may also be used to determine current delivery within preprogrammed settings. For example, some patients may tolerate higher levels of current during sleep, while others have a higher tolerance during activity.

The lead system used in the present embodiment may have a built-in vascular access port as oncology patients frequently have either subcutaneous or transcutaneous ports in place to minimize the number of new IV placements. In a preferred embodiment, a vascular access port has a means for removing the device during bathing and combination units using a drug pump or vascular access should be water resistant or waterproof.

Figure 19:
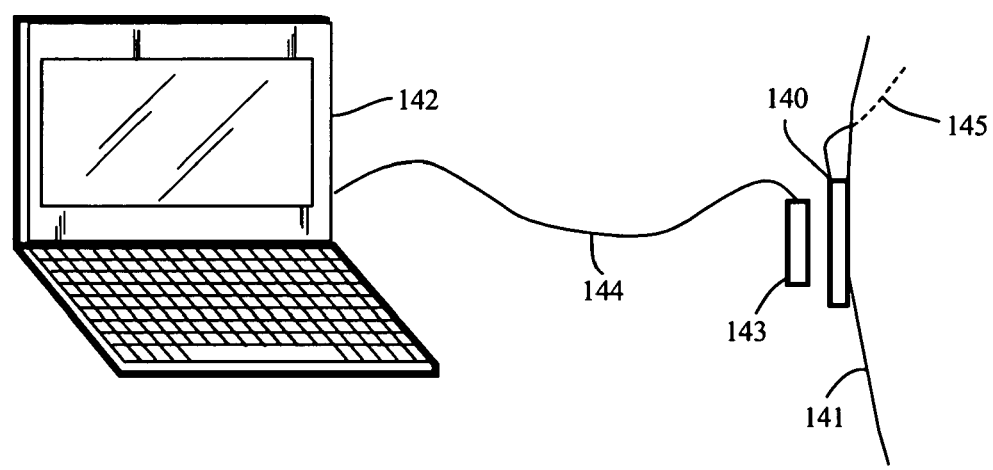
FIG. 19 is a schematic of an external generator adjacent to a body surface having a transcutaneous lead system.

Shown in FIG. 19 is an external generator 140 adjacent to a body surface 141 with a transcutaneous lead system 145. Shown are the external generator 140, the body surface 141, an instrument 142, a pod 143, a wire 144, and the transcutaneous lead system 145. The instrument 142 is coupled to the pod 143 by way of wire 144. As shown in FIG. 19, the instrument 142 is a laptop computer. However, the instrument 142 may be any number of useful pieces of equipment including for example a second high powered generator for the production of electroporation pulses. The pod 143 communicates with the generator 140 by a hardwired or wireless communication pathway. Coupled to the generator 140 is the transcutaneous lead system 145 for delivering electrical therapy to body tissue (not shown). The transcutaneous lead system 145 is implanted below the body surface 141.

The instrument 142 may control or power the generator 140 and/or receive information from the generator 140 by way of the pod 143. Alternatively, in another embodiment, the instrument 142 may be hardwired to the generator 140 without the use of the pod 143; this may be accomplished by plugging the wire 144 directly into the external generator 140. In yet another embodiment, the lead system 145 may connect directly to the instrument 142 without the use of the pod 143, the wire 144, or the generator 140. Clinics and/or hospitals may find the use of the instrument 142 hardwired to the lead system 145 advantageous over some of the other methods described hereinabove due to the reduction of required equipment. However, it should be understood that any of the equipment described herein may be used in any combination useful for the treatment of cancer.

Figure 20:
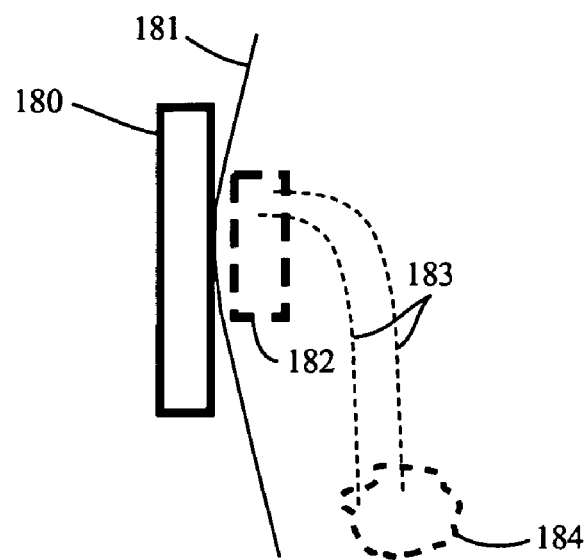
FIG. 20 is a drawing of an external generator having an implanted generator portion.

Turning now to FIG. 20, an external generator 180 having an implanted generator portion 182 is depicted. Shown are the external generator 180, a body surface 181, implanted generator portion 182, leads 183, and a tumor environment 184. The external generator 180 lies adjacent to the body surface 181 and the implanted generator portion 182 is implanted below the body surface 181. Leads 183 are coupled to the implanted generator portion 182 below the surface of the body surface 181. The distal ends of the leads 183 are implanted into the tumor environment 184. In a split formation, the external generator 180 with an implantable portion 182 is advantageously more versatile. For example, the implanted portion 182 may be reduced in size, thereby decreasing burden on the patient. In one embodiment, the power supply (not shown) and the controls (not shown) reside in the external generator 180 while the implanted portion 182 relays inputs to leads 183 and sends data out to the generator 180. In a preferred embodiment, power is inductively transferred from the external generator 180 which is outside the patient's body to the implanted portion 182 which is inside the patient's body. Alternatively, in another embodiment, the power supply for portion 182 is completely within the implanted generator portion 182.

Figure 21:
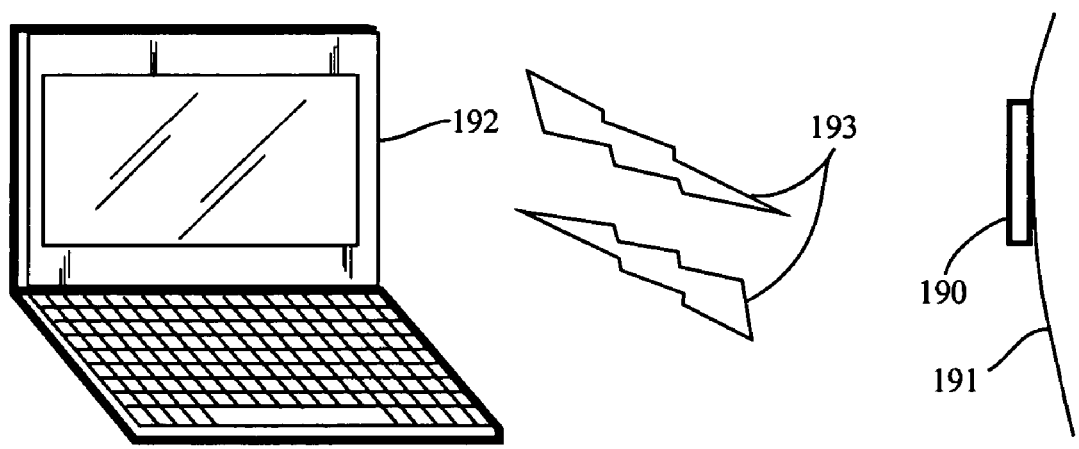
FIG. 21 is a schematic of an instrument for transmitting and receiving information to and from an external generator.

Shown in FIG. 21 is an instrument 192 for transmitting and receiving information to and from an external generator 190. Shown are the external generator 190, a body surface 191, instrument 192, and communication path 193. The external generator 190 is placed outside the body surface 191. The instrument 192 is also located outside the body surface 191 at some distance away from the external generator 190. The instrument 191 sends control information to the generator 190 by way of the communication path 193 which may be hardwired and/or wireless communication. Examples of wireless communication include, for example, radio, light, and/or sound. The generator 190 may also send information back to the instrument 192 by way of the communication path 193. All relevant therapy parameters, memory, and diagnostic data can be stored in the instrument 192.

Figures 22A, 22B:
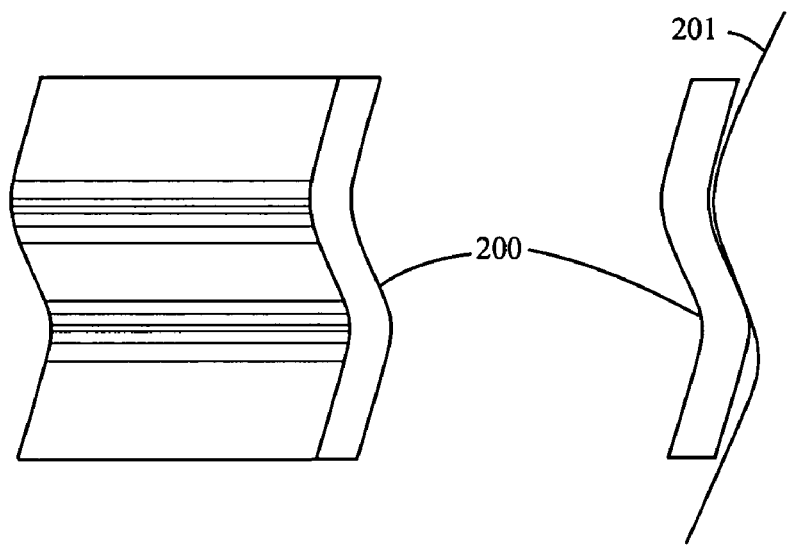
FIGS. 22a and 22b are illustrations of a flexible and/or curved generator.

Depicted in FIGS. 22a and 22b are two views of a flexible and/or curved generator. Shown are the generator 200 and a body surface 201. Because most body surfaces are curved, an external generator may be designed with a curve or may be sufficiently flexible to conform to most body curves for the comfort of a patient. FIG. 22a is a perspective view of the curved and/or flexible generator 200. FIG. 22b is a side view of the curved and/or flexible generator 200 adjacent to the body surface 201. The generator 200 may be designed to be bent to fit a curve and then to retain that shape until bent back to another shape. The generator 200 (and/or any other external generator disclosed herein) may be disposable, i.e. designed for one or a few uses and then discarded.

Figure 23:
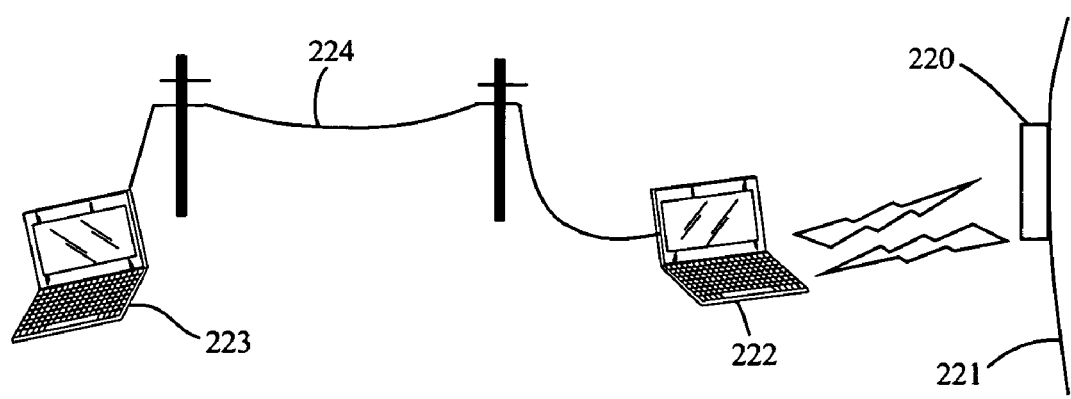
FIG. 23 is a representation of an instrument for communicating remotely with an external generator.

Illustrated in FIG. 23 is an instrument 222 for communicating remotely with an external generator 220. Shown are the external generator 220, a body surface 221, the local instrument 222, a remote instrument 223, and a communication line 224. The local instrument 222 for sending and receiving data from the external generator 220 (such as depicted in FIG. 21) may communicate with the remote instrument 223. As shown, data from instrument 222 may be sent to remote instrument 223 by way of a communication line 224. The communication line 224 may be a telephone wire, a cable, a wireless communication line and/or any other type of communication means. Data may be sent through email. The data may consist of therapy progress reports, which may include sensor readings and waveforms. Additionally, the external generator 220 may send warnings to the remote instrument 223 by way of the local instrument 222 and communication line 224 in the case of lead dislodgement and or low battery life.

Alternatively, the remote instrument 223 may send information back to the local instrument 222 and may, therefore, control the external generator 220 via local instrument 222. The local instrument 222 may control the external generator 220 by any controlling means, such as controlling means known by those of ordinary skill in the art, such as those described hereinabove. Thus, a medical practitioner located some distance away may modify the operation of a remote external generator 220 treating cancer.

Figure 24:
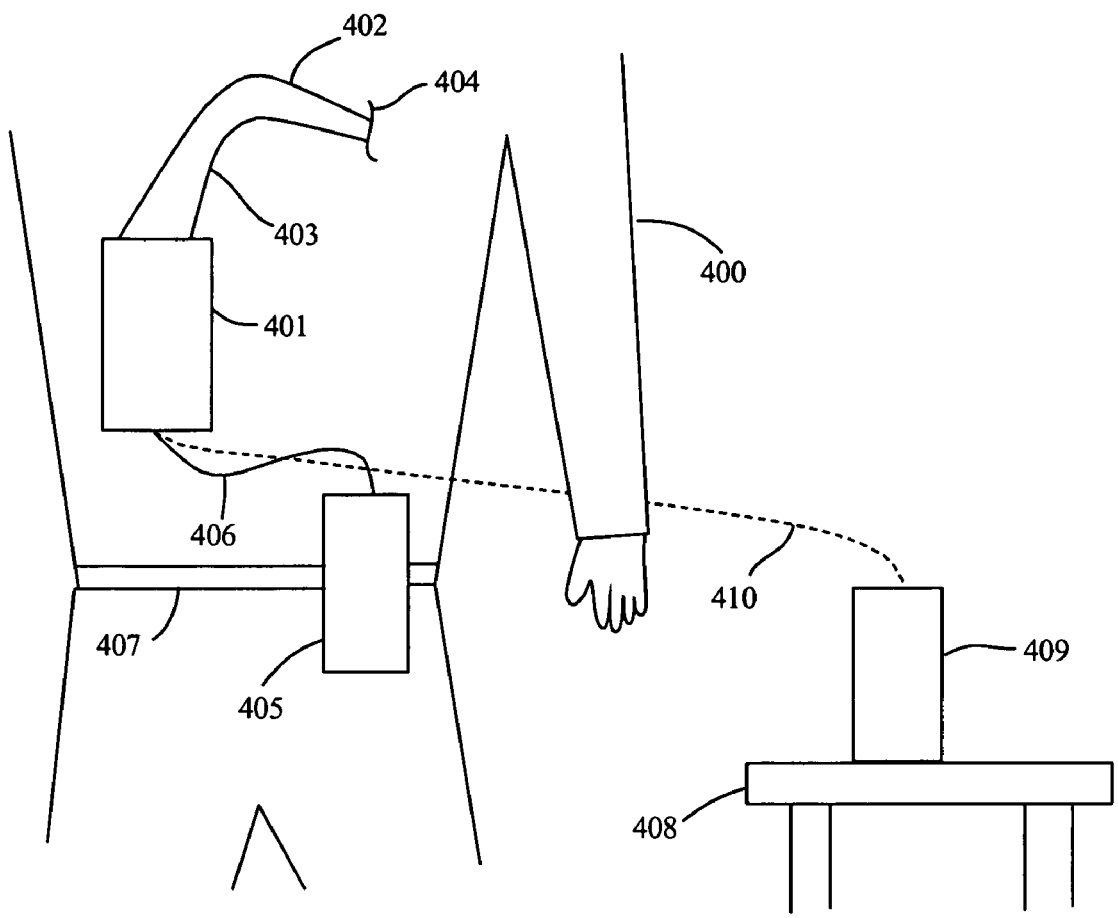
FIG. 24 is a representation of a human body having an external generator coupled thereto for the electrical treatment of cancer.

FIG. 24 is a representation of a human body 400 having an external generator 401 coupled thereto for the electrical treatment of cancer. Shown are the human body 400, the external generator 401, a first lead 402, a second lead 403, a location 404, a power source 405, a cable 406, a belt 407, a table 408, a power source 409, and a second cable 410.

The external generator 401 comprises at least one lead, in this case a first lead 402 and a second lead 403, pass into the human body 400 at a location 404. The first lead 402 and the second lead 403 are implanted adjacent to or into a tumor environment (not shown). The power source 405, which may be worn advantageously on the belt 407 (although it may be located in any convenient position), may entirely or partially power the external generator 401 by way of the cable 406.

As an alternative to the power source 405 located on the body, the external generator 401 may be coupled to a second (or alternative) power source 409 located remotely, such as on a table 408 by way of the second cable 410 (represented as a broken line). The power sources 405 and 409 may comprise, for example, a primary battery, a rechargeable battery, other electrical source, and the like.

Separating the external generator 401 from the power sources 405 and 409 advantageously decreases the weight of the external generator 401 and allows weight to be distributed at comfortable and convenient locations for the patient. Power sources 405 and 409 may be easily replaced if and when they are depleted and may have provisions for changing the energy sources without interrupting the supply of power to the external generator 401.

Figure 25:
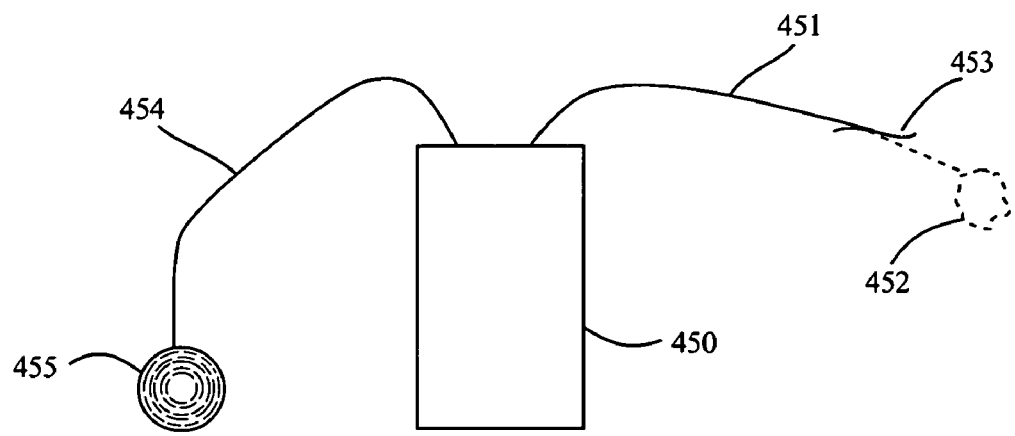
FIG. 25 is a drawing of an external generator having a tapered indifferent electrode.

FIG. 25 is a drawing of an external generator 450 having a tapered indifferent electrode 455. Shown are the external generator 450, a first lead 451, a tumor 452, an incision 453, a second lead 454, and the indifferent electrode 455. The external generator 450 is coupled to a first lead 451 passing into the tumor 452 through the incision 453. The second lead 454 is coupled to the indifferent electrode 455. Although depicted as a flat circular disk, the electrode 455 may assume other shapes, such as ovals, semi-circles, or rectangles, for example. The electrode 455 makes contact with the body but is designed of a material (such as carbon-impregnated rubber) whose impedance increases radially from its center to its circumference. This material may also be applied to other indifferent electrodes, such as those of FIGS. 2a and 12. The purpose of the tapered impedance is the minimization of any edge effects that may tend to burn or otherwise injure the body. The surface area of an indifferent electrode may range from 3 $cm^2$ to 100 $cm^2$.

All references cited herein are incorporated by reference.

What is claimed is:

1. A medical device for the treatment of abnormal tissue growth within a patient's body comprising:
    an external generator placed outside the body for providing an electrical pulse effective to carry out direct current ablation;
    at least one electrode transcutaneously placed in a body wherein said at least one electrode is operably coupled to said external generator such that said external generator delivers said electrical pulse to said at least one electrode to carry out direct current ablation of the abnormal tissue growth; and
    an affixing means for securing said external generator to the body;
    wherein the generator is sufficiently flexible to conform to an exterior surface of the patient's body.

2. The device of claim 1 further comprising a port located at a surface of the patient's body for releasably coupling the external generator to the electrode.

3. The device of claim 1 wherein the generator is equipped with quick connect means for releasably coupling its generator to a plurality of leads.

4. A medical device for the treatment of abnormal tissue growth within a patient's body comprising:
    an external generator placed outside the body for providing an electrical pulse effective to carry out direct current ablation;
    at least one electrode transcutaneously placed in a body wherein said at least one electrode is operably coupled to said external generator such that said external generator delivers said electrical pulse to said at least one electrode to carry out direct current ablation of the abnormal tissue growth;
    an affixing means for securing said external generator to the body; and
    a tapered indifferent electrode coupled to the generator and positioned on an exterior surface of the body, the indifferent electrode having an impedance that increases radially from its center to its circumference.

5. The device of claim 4 further comprising a port located at a surface of the patient's body for releasably coupling the external generator to the transcutaneously placed electrode.

6. The device of claim 4 wherein the generator is equipped with quick connect means for releasably coupling its generator to a plurality of leads.

* * * * *

UNITED STATES PATENT AND TRADEMARK OFFICE
CERTIFICATE OF CORRECTION

PATENT NO. : 7,720,549 B2  Page 1 of 1
APPLICATION NO. : 10/819641
DATED : May 18, 2010
INVENTOR(S) : Schroeppel et al.

It is certified that error appears in the above-identified patent and that said Letters Patent is hereby corrected as shown below:

On the TITLE PAGE:
Under (74) Attorney, Agent, or Firm – Please change "Thomas F. Lebens; Sinsheimer Juhnke Leben & McIvor, LLP" to --Thomas F. Lebens; Sinsheimer Juhnke Lebens & McIvor, LLP--.

Signed and Sealed this

Seventh Day of September, 2010

David J. Kappos
*Director of the United States Patent and Trademark Office*